(12) United States Patent
Matsumura et al.

(10) Patent No.: US 6,389,309 B1
(45) Date of Patent: May 14, 2002

(54) BIOLOGICAL SIGNAL TRANSMISSION APPARATUS

(75) Inventors: Fumiyuki Matsumura; Tetsushi Sekiguchi; Hiroshi Sakata; Hidehiro Hosaka, all of Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/657,630

(22) Filed: Sep. 8, 2000

Related U.S. Application Data

(62) Division of application No. 09/220,751, filed on Dec. 28, 1998, now Pat. No. 6,161,036.

(30) Foreign Application Priority Data

Dec. 25, 1997 (JP) .............................. 9-358536
Dec. 26, 1997 (JP) .............................. 9-359933

(51) Int. Cl.[7] .......................................... A61B 5/0402
(52) U.S. Cl. ............................................... 600/509
(58) Field of Search .............................. 600/508, 509, 600/382, 393; 128/903

(56) References Cited

U.S. PATENT DOCUMENTS

| | | | |
|---|---|---|---|
| 5,311,873 A | * | 5/1994 | Savard et al. ............... 600/509 |
| 5,749,365 A | | 5/1998 | Magil |
| 5,862,803 A | | 1/1999 | Besson et al. |
| 6,161,038 A | * | 12/2000 | Schookin et al. ........... 600/509 |

FOREIGN PATENT DOCUMENTS

| | | |
|---|---|---|
| JP | 60-97103 | 7/1985 |
| JP | 62-202804 | 12/1987 |
| JP | 63-32501 | 3/1988 |
| JP | 6-77846 | 3/1994 |
| JP | 9-108194 | 4/1997 |

\* cited by examiner

Primary Examiner—George R. Evanisko
(74) Attorney, Agent, or Firm—Sughrue Mion, PLLC

(57) ABSTRACT

An electrode 4 for detecting a biological signal and a loop antenna 3 are integrally mounted on a support 2 placed on the surface of a living body and a transmitter 5 is placed on the support 2. A biological signal detected on the electrode 4 is input through a connector 11 to electric circuitry 10 of the transmitter 5 and an electric signal processed by the electric circuitry 10 is output through connectors 12 and 13 to both ends of the loop antenna 3 from which the biological signal is emitted to a receiver. At this time, the opening face of the loop antenna 3 is in a direction almost perpendicular to the surface of a living body for improving sensitivity.

10 Claims, 34 Drawing Sheets

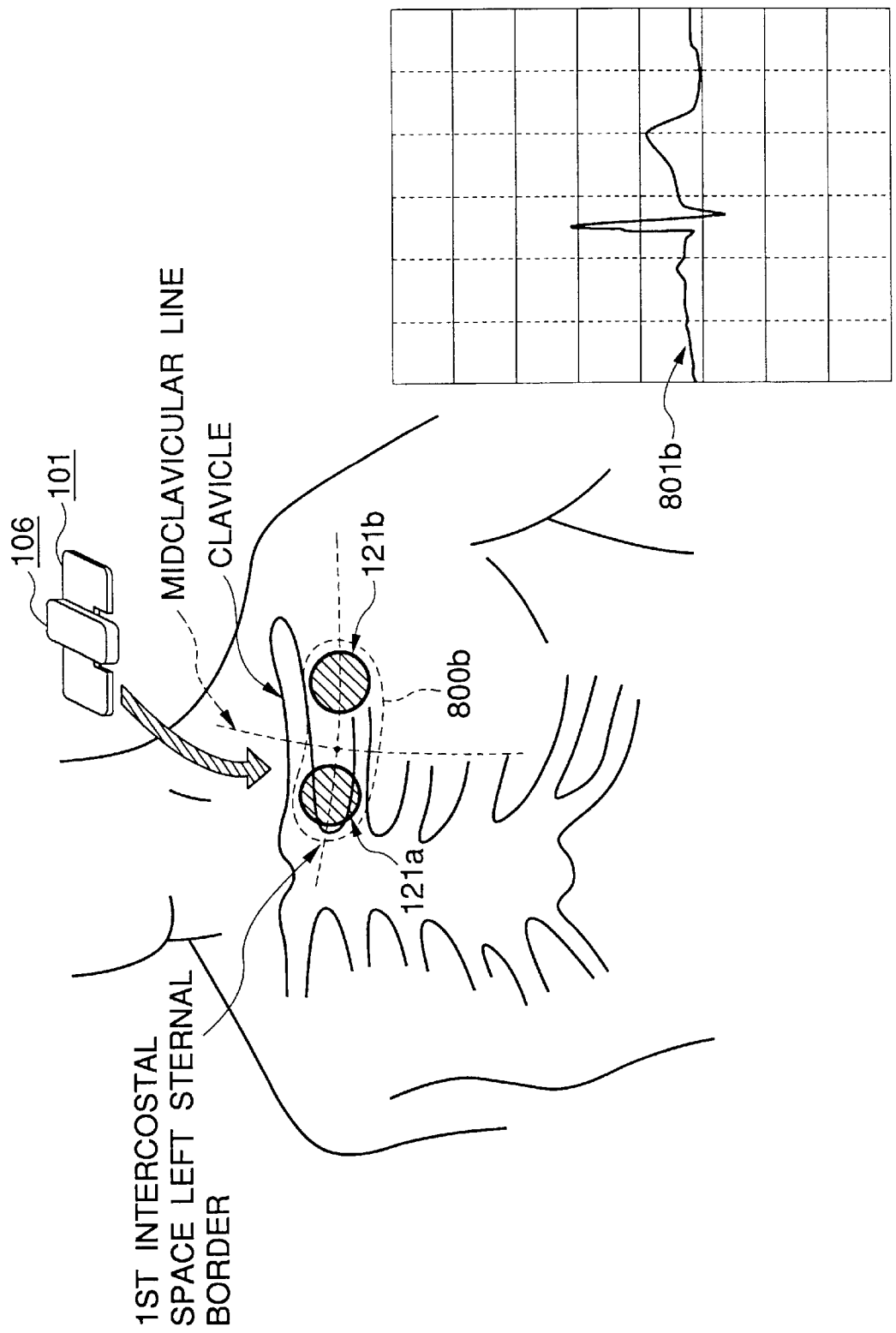

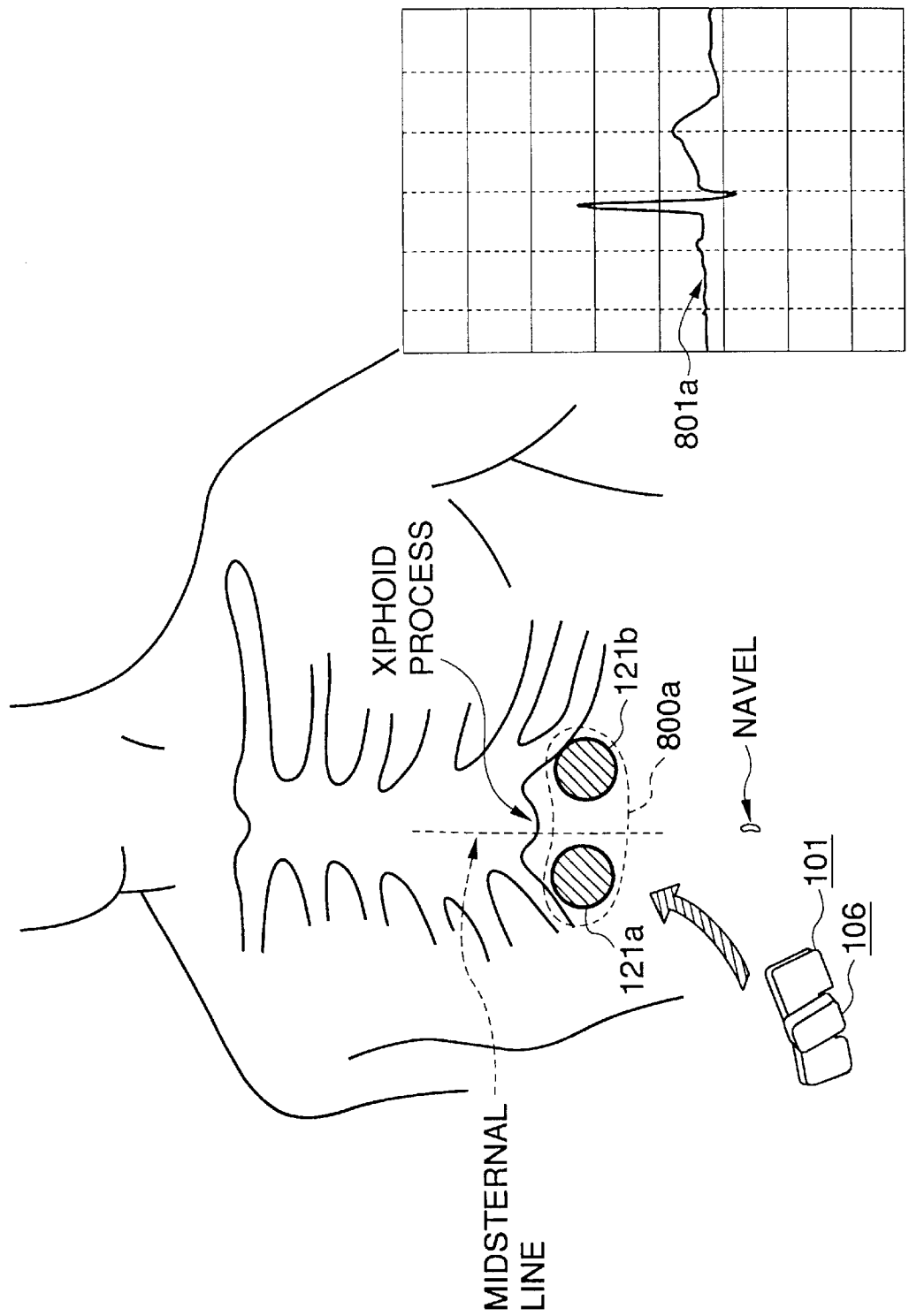

BIOLOGICAL SIGNAL TRANSMISSION APPARATUS

This is a divisional of application Ser. No. 09/220,751 filed Dec. 28, 1998, now U.S. Pat. No. 6,161,036 the disclosure of which is incorporated herein by reference.

BACKGROUND OF THE INVENTION

1. Field of the Invention

This invention relates to a biological signal transmission apparatus of a medical telemeter for transmitting a biological signal from a transmitter through an antenna to a receiver and in particular to a biological signal transmission apparatus using a loop antenna, a microstrip antenna as an antenna.

2. Related Art

A system for transmitting by radio a biological signal detected on an electrode placed on a subject to a nearby computer diagnostic apparatus, etc., via an antenna for diagnosis is known. Hitherto, various propositions have been made as a transmission apparatus used with such a system.

In a proposition described in JP-A-60-97103U, two electrodes 502 and 503 attached to a chest belt 501 and a transmitter main unit 504 placed on a wrist of a subject are connected by electrode leads 505 and 506, as shown in FIG. 34. An antenna line 507 from the transmitter main unit 504 is placed closely on the leads 505 and 506 in parallel therewith and an end of the antenna line 507 is buried in the chest belt 501. The electrode leads 505 and 506 and the antenna line 507 are insulated from each other and the end of the antenna line 507 is also electrically insulated so as not to touch the body surface of the subject.

According to the proposition, the antenna line 507 is placed closely on the leads 505 and 506 and thus can be made 1 m or longer without disturbing any motion, and the efficiency of the transmitter 504 can be improved and miniaturized for enhancing portability of the transmitter.

In a proposition described in JP-A-62-202804U, a pair of electrodes 201 and 202 is placed in unit cases 203 and 204, which are opened at bottoms for exposing the electrodes 201 and 202, and both ends of an antenna line 205 are connected to the electrodes 201 and 202, as shown in FIG. 35. The unit cases 203 and 204 are coupled by a connection cable 206 and the antenna line 205 is inserted into the connection cable 206.

According to the proposition, the electrodes 201 and 202 placed in a pair of unit cases 203 and 204 are fitted to a heart rate detection part of a living body and a signal from the antenna line 205 is transmitted, so that the device is easily attached and detached and moreover can be placed without an oppressive feeling or a feeling of wrongness on the chest of the subject.

In a proposition described in JP-A-63-32501U, a device comprises a pair of electrodes 301 and 302, a transmitter main unit 303 having electric circuitry for processing an electrocardiographic signal detected on the electrodes 301 and 302, and an antenna 304 for sending the resultant signal to a receiver by a radio wave, as shown in FIG. 36. The antenna 304 is covered with water-repellent fibers and is put on the surface of a human body.

According to the proposition, the antenna 304 is covered with water-repellent fibers and is connected to the transmitter main unit 303 so that it is put on the surface of a human body. Thus, when the device is attached to a subject, clothes of the subject do not swell locally and moreover it is not feared that the electrode 301, 302 may be off the attachment point. Resultantly, sufficiently strong radio waves can be sent to the receiver in addition to ease of use.

In a proposition described in JP-A-9-108194, a base sheet 401 placed on the anterior chest wall of a subject is formed like an L letter, a longwise portion 401a is put along the breast bone line of the subject, and a widthwise portion 401c is directed toward the heart side from a corner 401b positioned near the xiphisternum of the subject, as shown in FIG. 37. The base sheet 401 is formed on a rear with an adhesion layer made to adhere to the anterior chest wall. A first electrode 402 is attached in the proximity of the corner 401b, a second electrode 403 is attached in the proximity of the upper end part of the longwise portion 401a, and a third electrode 404 is attached in the proximity of a side end part of the widthwise portion 401c. Further, a fourth electrode 405 is attached slantingly below the second electrode 403 and a fifth electrode 406 is attached above the third electrode 404.

Of the five electrodes arranged as described above, α induction is detected between the electrodes 402 and 403 and β induction is detected between the electrodes 403 and 404. Δ induction for ischaemia of side and front and rear walls in a high-potential direction weak in sensitivity only with a induction and β induction is detected by means of the electrodes 405 and 406. The electrocardiographic signals induced to the electrodes are amplified and modulated by a circuit unit 407 attached to the base sheet 401 and are transmitted to the receiver through an antenna 408 attached along the longwise portion 401a.

According to the proposition, the electrodes 402 to 406, the circuit unit 407, and the antenna 408 are mounted integrally on the base sheet 401, so that the device is easily placed on the subject and action is not limited.

In the examples in the related arts described above, the antennas are monopole antennas using the electricity length of a quarter the wave length. For example, assuming that the transmission frequency is 300 MHz, the wave length is 1 m and the antenna length becomes 25 cm. To place the monopole antenna so that it is not affected by a human body as much as possible, the monopole antenna may be placed in a direction perpendicular to the surface of a human body and distant from the human body. However, the antenna length is long (in this case, 25 cm), thus when the transmitter is placed on a human body, it disturbs the motion of the human body. If the transmitter is placed along the surface of the human body so as to facilitate the motion, radio waves radiated from the antenna are affected by the human body as described above, thus the gain is easily degraded. Also, although employing small and compact transmitter and electrode, there is still a problem that long using for standard limb lead (II) between electrodes disturb patient.

SUMMARY OF THE INVENTION

It is therefore an object of the invention to provide a small-sized biological signal transmission apparatus that can emit a biological signal detected on an electrode placed on the surface of a living body to a receiver with stable and good sensitivity and can be easily placed on the living body.

According to an aspect of the present invention, there is provided a biological signal transmission apparatus comprising an electrode for detecting a biological signal, a support for supporting the electrode, the support being placed on a living body surface, a transmitter having electric circuitry for processing the biological signal detected on the electrode, and at least one loop antenna for emitting the biological signal processed by the electric circuitry to a receiver, the loop antenna being disposed so that an opening face is placed in a direction almost perpendicular to the living body surface.

According to another aspect of the present invention, there is provided a biological signal transmission apparatus comprising an electrode for detecting a biological signal, a support for supporting the electrode, the support being placed on a living body surface, a transmitter having electric circuitry for processing the biological signal detected on the electrode, and two loop antennas for emitting the biological signal processed by the electric circuitry to a receiver, the loop antennas being disposed so that opening faces are placed in a direction almost perpendicular to the living body surface and are almost at right angles to each other.

According to another aspect of the present invention, in the biological signal transmission apparatus, at least one of the loop antennas is contained in the transmitter.

According to another aspect of the present invention, in the biological signal transmission apparatus, at least one of the loop antennas is divided into two parts, one loop antenna division part is placed in the support and the other is placed in the transmitter, and the transmitter is placed on the support, thereby putting the loop antenna division parts into one piece.

According to another aspect of the present invention, in the biological signal transmission apparatus, the loop antenna is integral with the support and is connected at both ends to output of the electric circuitry through connection members and the transmitter is placed on the support.

According to another aspect of the present invention, there is provided a biological signal transmission apparatus comprising an electrode for detecting a biological signal, a support for supporting the electrode, the support being placed on a living body surface, a transmitter having electric circuitry for processing the biological signal detected on the electrode, at least one loop antenna for emitting the biological signal processed by the electric circuitry to a receiver, the loop antenna being disposed so that an opening face is placed in a direction almost perpendicular to the living body surface, and a microstrip antenna having a radiation plate and a base plate opposed in parallel with the living body surface, the base plate being placed nearer to the living body surface.

According to another aspect of the present invention, there is provided a biological signal transmission apparatus comprising an electrode for detecting a biological signal, a support for supporting the electrode, the support being placed on a living body surface, a transmitter having electric circuitry for processing the biological signal detected on the electrode, two loop antennas for emitting the biological signal processed by the electric circuitry to a receiver, the loop antennas being disposed so that opening faces are placed in a direction almost perpendicular to the living body surface and are almost at right angles to each other, and a microstrip antenna having a radiation plate and a base plate opposed in parallel with the living body surface, the base plate being placed nearer to the living body surface.

In the biological signal transmission apparatus of the present invention, at least one of the loop antennas and the microstrip antenna is contained in the transmitter.

In the biological signal transmission apparatus of the present invention, at least one of the loop antennas and the microstrip antenna is integral with the support and the loop antenna or the microstrip antenna is connected to output of the electric circuitry through a connection member and the transmitter is placed on the support.

BRIEF DESCRIPTION OF THE DRAWINGS

In the accompanying drawings:

FIG. 38 is a front view of the water-containing gels positioned through midclavicular line and parallel to a clavicle; and FIG. 39 is a front view of the water-containing gels attached on a chest defiend between a xiphoid process and a navel through and perpendicular to a midsternal line.

DETAILED DESCRIPTION OF THE PREFERRED EMBODIMENTS

Figure 1:
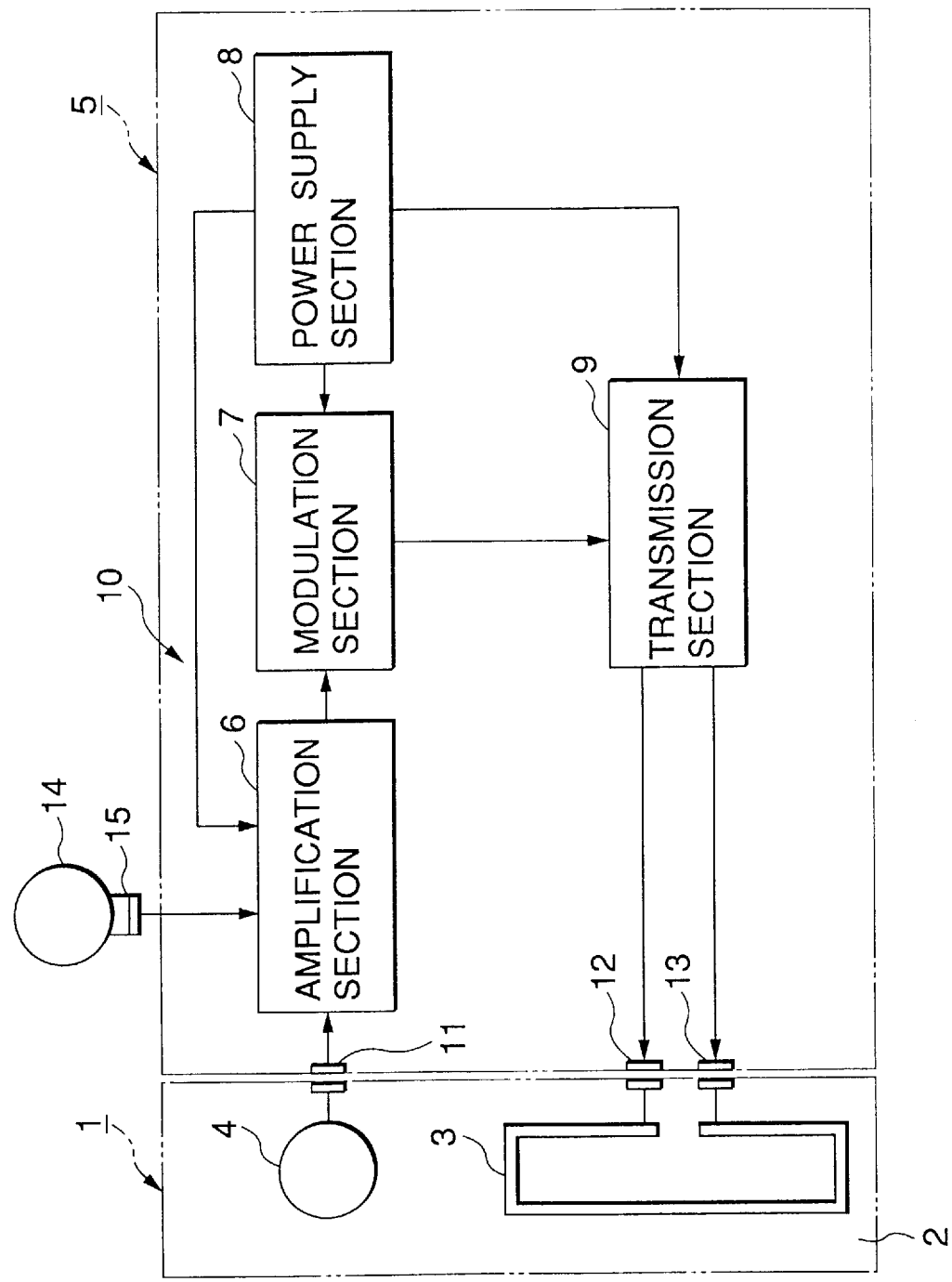
FIG. 1 is a block diagram to show a configuration example of a first embodiment of a biological signal transmission apparatus of the invention.
Figure 2:
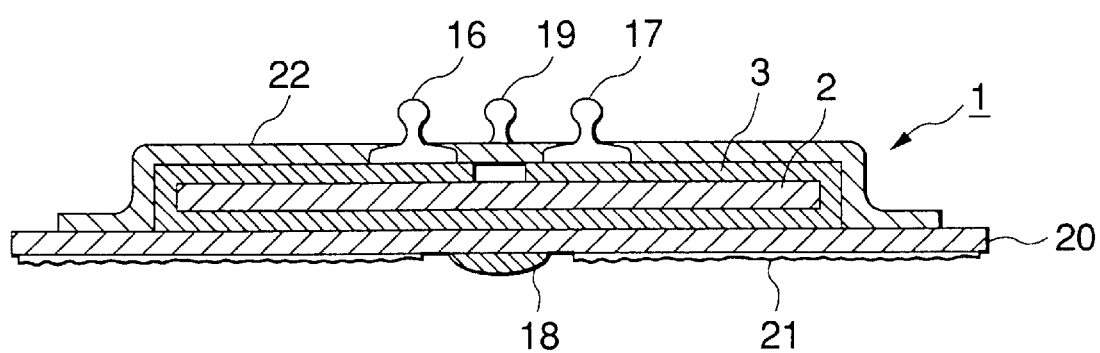
FIG. 2 is a longitudinal sectional view to show the configuration of a living body placement section in FIG. 1.
Figure 3:
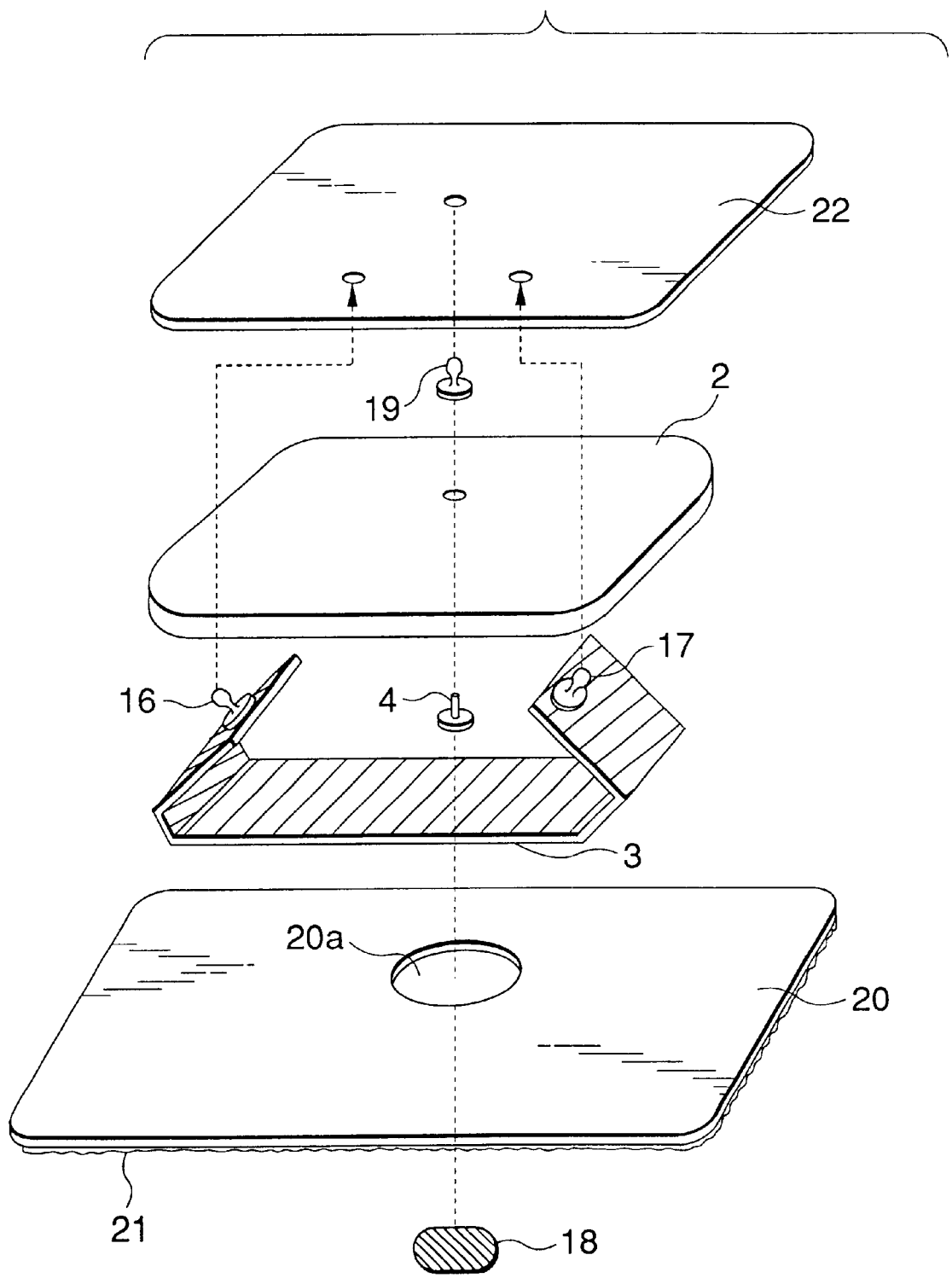
FIG. 3 is an exploded perspective view of the living body placement section shown in FIG. 2.
Figure 4:
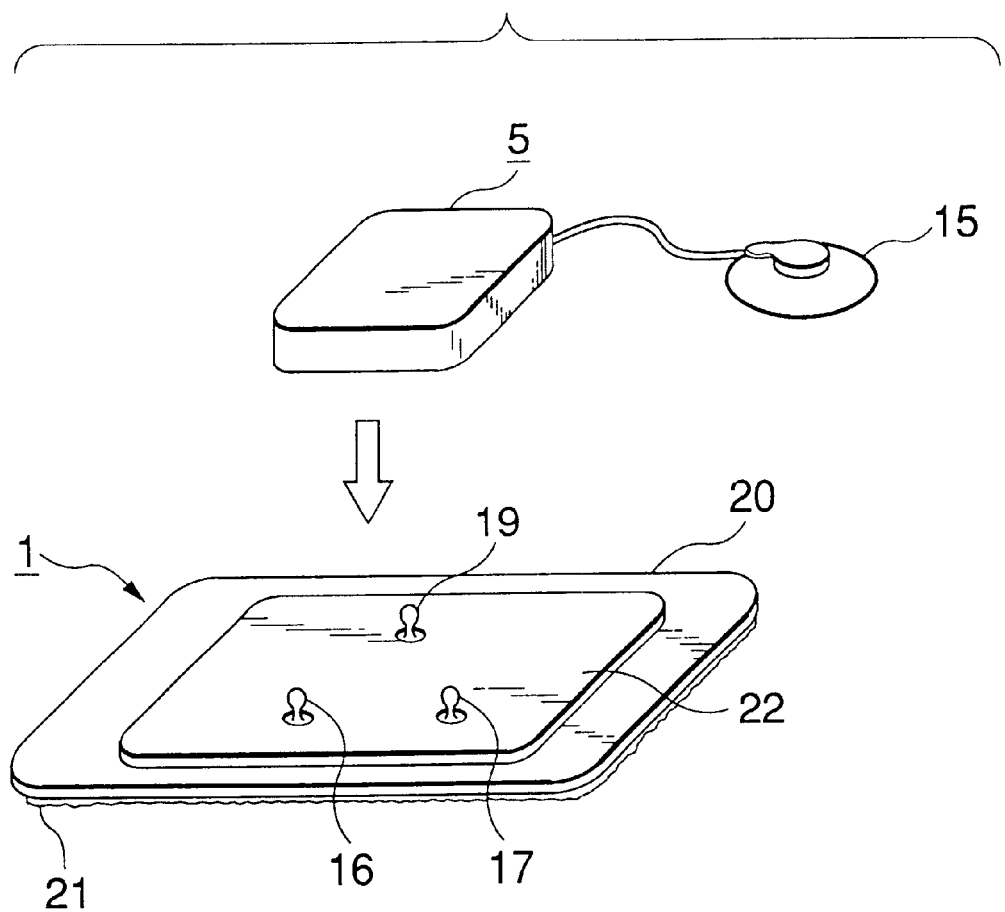
FIG. 4 is an external perspective view of the living body placement section and a transmitter in FIG. 1.

Referring now to the accompanying drawings, there are shown preferred embodiments of a biological signal transmission apparatus of the invention. FIG. 1 is a block diagram to show a configuration example of a first embodiment of the invention. FIG. 2 is a longitudinal sectional view to show the configuration of a living body placement section in FIG. 1. FIG. 3 is an exploded perspective view of the living body placement section shown in FIG. 2. FIG. 4 is an external perspective view of the living body placement section and a transmitter in FIG. 1.

In FIG. 1, a living body placement section 1 comprises a loop antenna 3 and an electrode 4 integrally mounted on a flat support 2 formed of an insulating material. A transmitter 5 comprises electric circuitry 10 made up of an amplification section 6, a modulation section 7, a power supply section 8, and a transmission section 9. The electrode 4 and the amplification section 6 and the loop antenna 3 and the transmission section 9 are electrically connected through connectors 11, 12, and 13. Numeral 14 is an electrode placed on another part of a living body. The electrode 14 is connected to the amplification section 6 by a connector 15.

Power is supplied from the power supply section 8 to the amplification section 6, the modulation section 7, and the transmission section 9. When the support 2 is placed on the living body surface of a subject, a biological signal detected on the electrode 4 is amplified by the amplification section 6 and is modulated by the modulation section 7, then is sent from the transmission section 9 to the loop antenna 3. The biological signal is transmitted by radio from the loop antenna 3 to a receiver (not shown).

In FIG. 2 and FIG. 3, the support 2 is formed of an insulating material like a square plate. The loop antenna 3 formed of a conductive material like a belt is placed along one side of the lower face of the support 2 and the loop antenna 3 is folded at both ends back to the upper face of the support 2 so as to sandwich the support 2. Convex hooks 16 and 17 forming a connector are fixed at both ends of the loop antenna 3.

The electrode 4 passes through the support 2 from the lower face thereof, projects upward, and is fixedly secured in the portion of the support 2 where the loop antenna 3 is not placed. Conductive water-containing gel 18 is applied to the lower end face of the electrode 4. A hook 19 is attached to one end of the electrode 4 passing through the support 2 from the lower face thereof and projecting upward. An insulating sheet 20 covering the loop antenna 3 is bonded to the full lower face of the support 2 and the electrode 4 is exposed to the lower face through a hole 20a made in the insulating sheet 20. An adhesive 21 is applied to the lower face of the insulating sheet 20. The upper face of the support 2 is also covered with an insulating sheet 22 and the hooks 16, 17, and 19 pass through the insulating sheet 22 and project upward.

Figure 30:
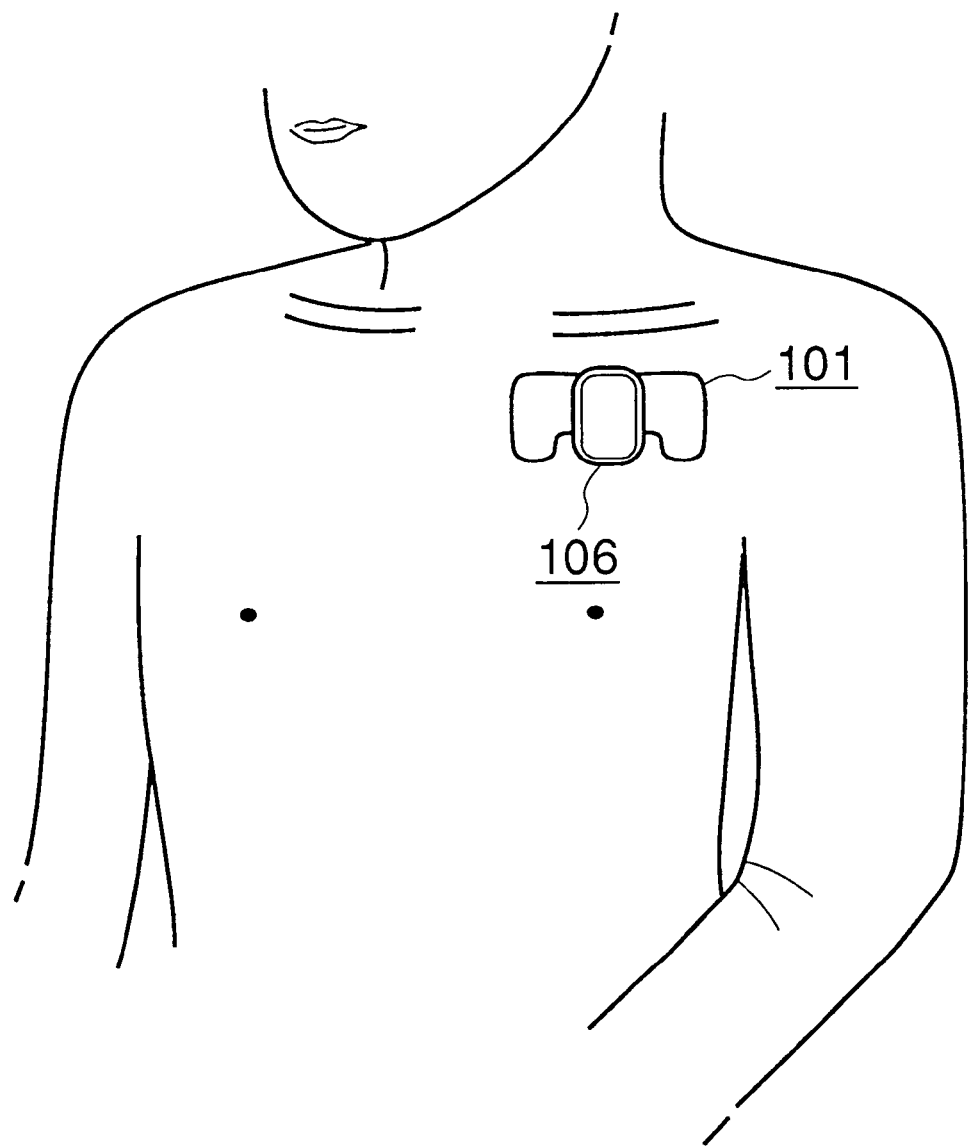
FIG. 30 is an illustration to show an example of placing the biological signal transmission apparatus of the invention on a living body.

The transmitter 5 is placed on and fixed to the described living body placement section 1, as shown in FIG. 4. At this time, the hooks 16, 17, and 19 are connected to the corresponding connectors (not shown) of the transmission section 9 and the amplification section 6 in the transmitter 5. As shown in FIG. 30, when the living body placement section 1 is bonded to the surface of the living body of a subject via the adhesive 21, a biological signal detected on the electrode 4 is sent through the hook 19 to the transmitter 5 and is processed by the electric circuitry 10 in the transmitter 5, then is sent through the hooks 16 and 17 to the loop antenna 3 from which the biological signal is transmitted to the receiver (not shown) by radio.

First Embodiment

Figure 5:
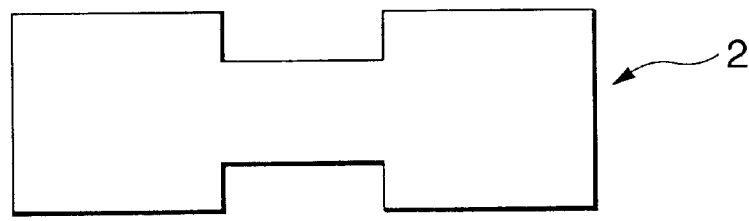
FIG. 5 is a plan view to show the form of a modified example of a support in FIG. 3.

Next, specific structures and materials of the parts of the first embodiment shown in FIG. 1 to FIG. 4 will be discussed in detail. The support 2 is several ten $\mu$m to several mm thick, for example, and has reasonable rigidity for holding the living body placement section 1. In the above-described example, the support 2 is shaped like a square plate, but may be of any shape like a center-constricted plate, for example, as shown in FIG. 5. For example, the support 2 is formed of a material of paper or a macromolecular dielectric substance, such as vinyl chloride, polyurethane, polystyrene, polycarbonate, polypropylene, fluororesin, silicone resin, cellulose acetate, polyester, rayon, nylon, vinylon, epoxy resin, or ceramics.

Figure 6:
FIG. 6 is a perspective view to show the structure of a loop antenna in FIG. 3.
Figure 7:
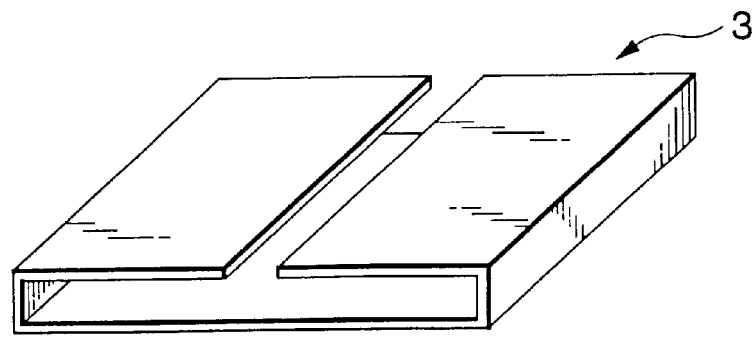
FIG. 7 is a perspective view to show the structure of a modified example of the loop antenna in FIG. 3.

The loop antenna 3 is several μm to several mm thick, for example, has a surrounding length of about several times the wavelength about a several tenths of the wave length, and is formed of an elongated conductive film. The planar shape is not limited; for example, the loop antenna 3 may be narrow as shown in FIG. 6 or may be wide as shown in FIG. 7. For example, metal, carbon, a macromolecular conductive substance, or resin to which conductive plating is given is used as the material of the loop antenna 3.

Figure 8:
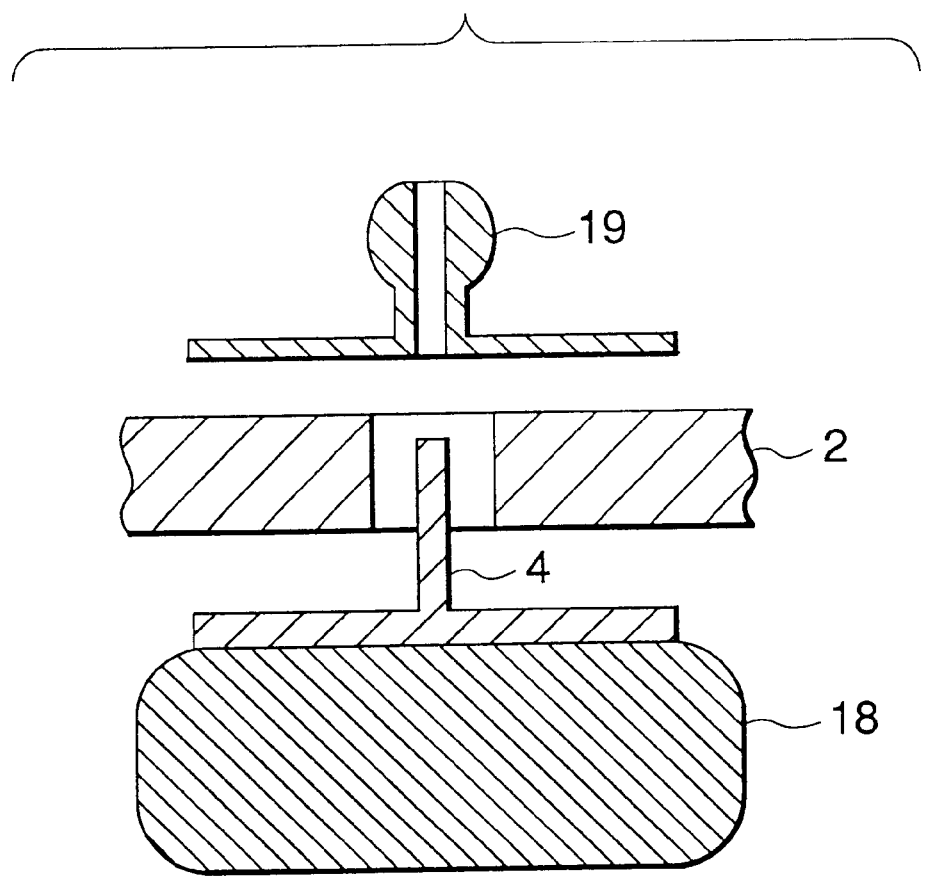
FIG. 8 is an exploded longitudinal sectional view to show the attachment structure of an electrode in FIG. 2 and FIG. 3.

The electrode 4 is fixed to the support 2 through the connector 11, is a conductive substance itself, and acts as an electrode for deriving a living body electricity phenomenon. It may be of any structure if it can be stably fixed to the hook 19 as the connector, for example, as shown in FIG. 8. The material of the electrode 4 may be a conductive substance similar to connector described later, and is not limited. For example, a macromolecular conductive substance, such as conductive rubber or water-containing resin, metal, such as copper, stainless steel, or aluminum, carbon, such as carbon fibers or graphite, resin to which conductive plating is given (for example, a conductive metal film of gold, silver, copper, nickel, aluminum, palladium, platinum, etc., is formed on the surface of a macromolecular insulating substance or a macromolecular conductive substance by means of sputtering evaporation, electrolytic plating, electroless plating, etc.,) is used as the material of the electrode 4.

The water-containing gel 18 makes electric conduction between the electrode 4 and a living body surface and preferably it has adhesion to a living body. For example, gelatin, polyacrylic acid, its salt, karaya gum, any other water-soluble or water-dispersable acrylic-family polymer, water-soluble or water-dispersable polymer of polyacrylamide, polyvinyl alcohol, carboxymethyl cellulose, polyurethane, etc., or the like can be named as the base material for forming the gel layer.

In the above-described example, the hooks 16, 17, and 19 are used as the parts forming the connectors 11, 12, and 13, but the scope of the invention is not limited to them. For example, a structure of a general-purpose electric connector, a contact-type connector, etc., may be used. A material similar to that of the electrode 4 described above can be used.

The insulating sheets 20 and 22 are provided so that a human body and the loop antenna 3 do not come in direct contact with each other. They may be made of any material if the material has an insulating property; the material is not limited.

The adhesive 21 is provided for strongly fixing the living body placement section 1 to a living body; preferably it is a substance not giving an impetus to the living body. For example, a known adhesive material excellent in intimate contact with the living body placement section 1, such as double-sided adhesive tape, an acrylic family, a rubber family, or a vinyl ether family, can be used.

According to the embodiment, the loop antenna 3 is placed near the surface of a living body through the support 2 and moreover the opening face of the loop antenna 3 is almost at right angles to the living body surface, so that the sensitivity can be improved and the gain can be increased because of the known loop antenna characteristics.

Second Embodiment

Figure 9:
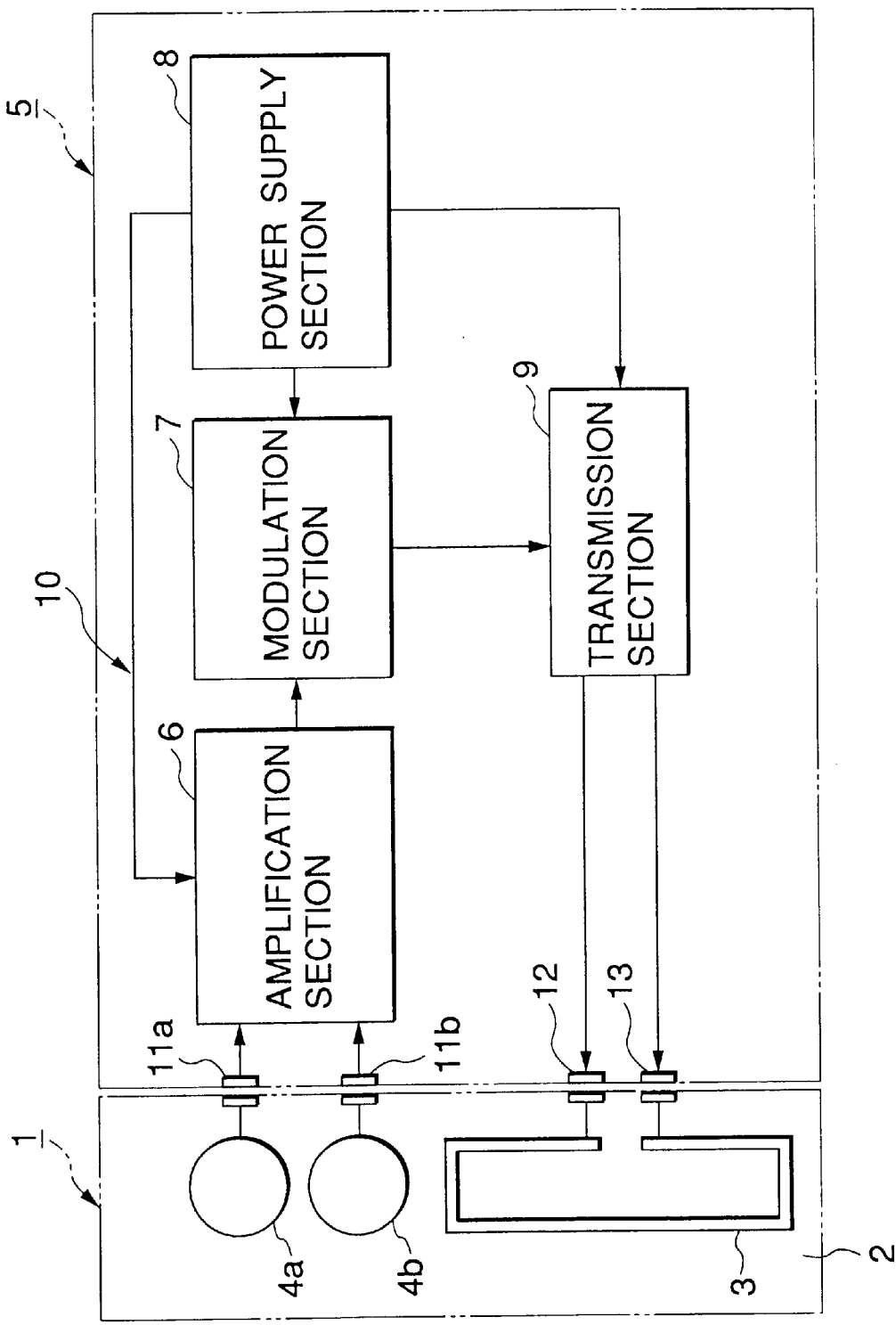
FIG. 9 is a block diagram to show a configuration example of a second embodiment of the invention.
Figure 10:
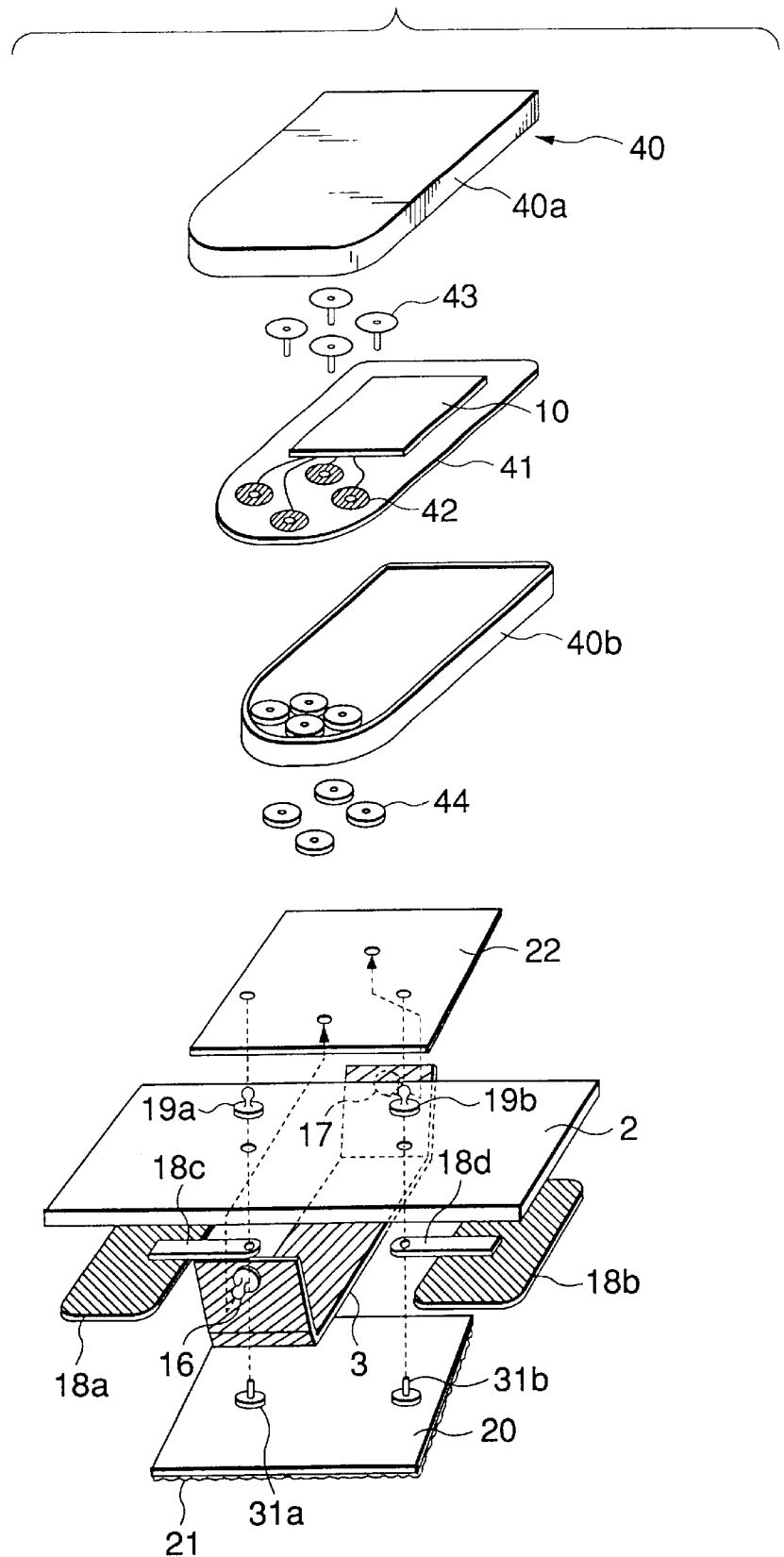
FIG. 10 is an exploded perspective view to show a configuration example of a living body placement section and a transmitter in FIG. 9.
Figure 11:
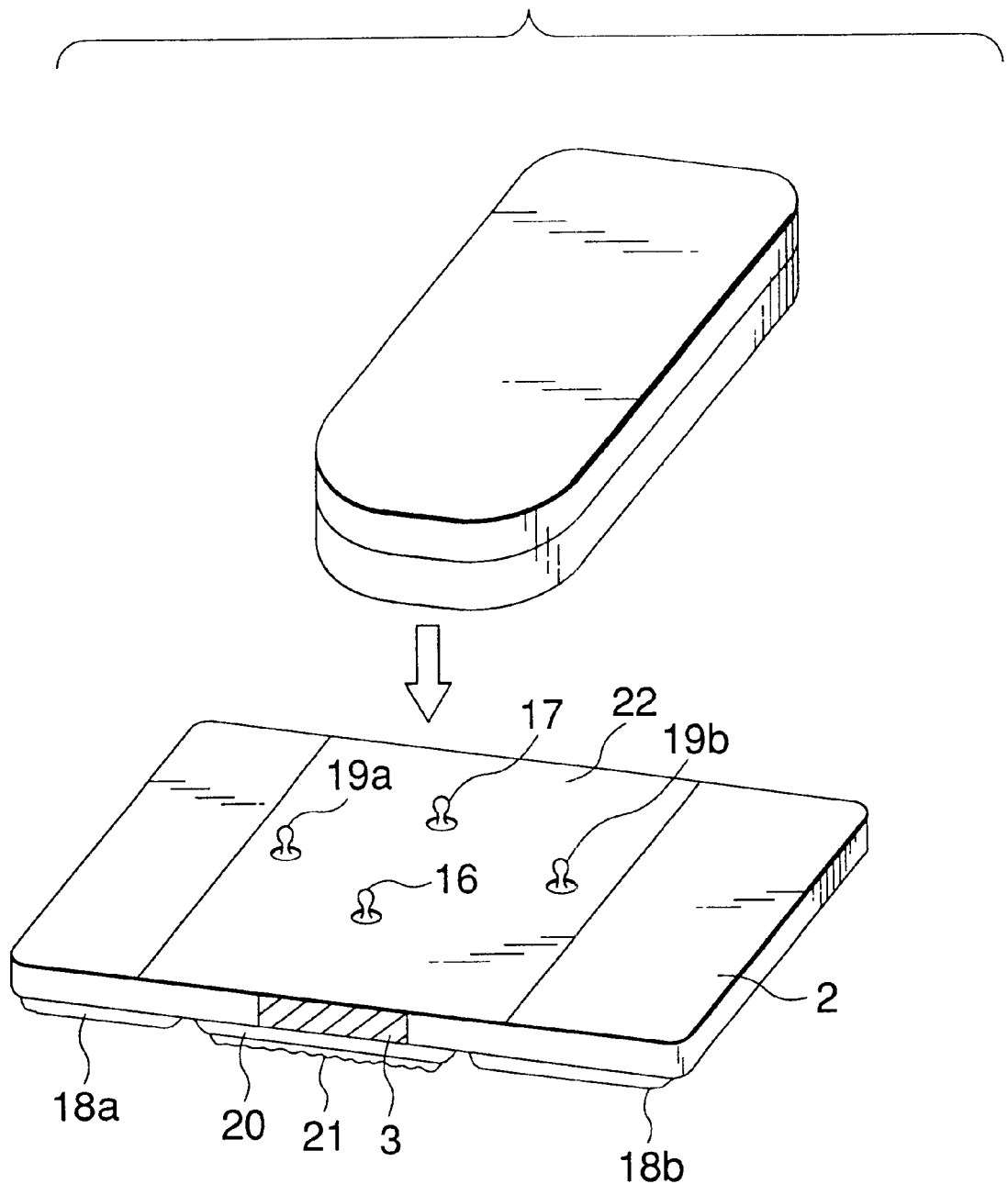
FIG. 11 is an external perspective view of the living body placement section and the transmitter in FIG. 9.

FIG. 9 to FIG. 11 show a configuration example of a second embodiment of the invention. Parts identical with or similar to those previously described with reference to FIG. 1 to FIG. 4 are denoted by the same reference numerals in FIG. 9 to FIG. 11 and will not be discussed again in detail.

In the second embodiment, the number of electrodes 4 is two and biological signals detected on electrodes 4a and 4b are sent through connectors 11a and 11b to an amplification section 6, as shown in FIG. 9. Other components and functions are almost similar to those of the first embodiment previously described with reference to FIG. 1 to FIG. 4.

FIG. 10 is an exploded perspective view to show a configuration example of a living body placement section 1 and a transmitter 5 in FIG. 9. FIG. 11 is an external perspective view of the living body placement section 1 and the transmitter 5 in FIG. 9. In FIG. 10, ends of conductive terminals 18c and 18d disposed on the lower face of a support 2 are electrically connected to caulking devices 31a and 31b respectively, and conductive water-containing gels 18a and 18b are attached to opposite ends of the conductive terminals 18c and 18d. The caulking devices 31a and 31b pass through the support 2 and project upward and are fixed to the support 2 together with the conductive terminals 18c and 18d.

A loop antenna 3 is placed on the lower face of the support 2 between the conductive terminals 18c and 18d and is folded at both ends back to the upper face of the support 2 so as to sandwich the support 2. An insulating sheet 20 for covering the loop antenna 3, the caulking devices 31a and 31b, and the conductive terminals 18c and 18d is bonded to the space between the conductive water-containing gels 18a and 18b on the lower face of the support 2, and an adhesive 21 is applied to the lower face of the insulating sheet 20.

The upper face of the support 2 is also covered with an insulating sheet 22. Convex hooks 19a and 19b placed at the upper ends of the caulking devices 31a and 31b and convex hooks 16 and 17 fixed to both ends of the loop antenna 3 pass through the insulating sheet 22 and project upward. A transmitter 5 is made up of an upper lid 40a and a lower lid 40b making up a cabinet 40, a board 41 housed therein, and electric circuitry 10 mounted on the board 41. The board 41 is formed on a surface with four lands 42 connected to the electric circuitry 10. It is fixed to the lower lid 40b through the lands 42 by a caulking device 43 and a concave hook 44. Also in the embodiment, as shown in FIG. 11, the transmitter 5 is placed on and fixed to a living body placement section 1 through the convex hooks 16, 17, 19a, and 19b and the concave hook 44, and the functions and advantages similar to those of the first embodiment previously described with reference to FIG. 1 to FIG. 4 can be provided. The structures and materials of the members shown in FIG. 9 to FIG. 11 are almost similar to those of the first embodiment previously described with reference to FIG. 1 to FIG. 4.

In the second embodiment, the number of the electrodes 4 is two, but three or more electrodes 4 may be used. In this case, the electrodes 4 are placed at appropriate positions of the living body placement section 1 and are related to the connectors 11 and the amplification section 6 and a modulation section 7 in the electric circuitry 10, whereby a large number of biological signals can be derived and amplified, then transmitted from a transmission section 9, needless to say.

Figure 12:
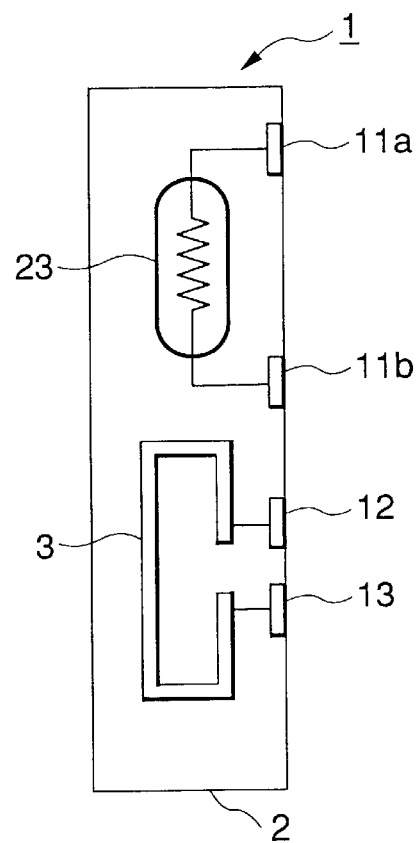
FIG. 12 is a block diagram of a living body placement section to show a configuration wherein electrodes in FIG. 9 are replaced with a transducer.

As shown in FIG. 12, the electrodes 4 are replaced with a transducer 23, whereby the temperature, blood pressure, etc., of a living body can also be detected.

Third Embodiment

Figure 13:
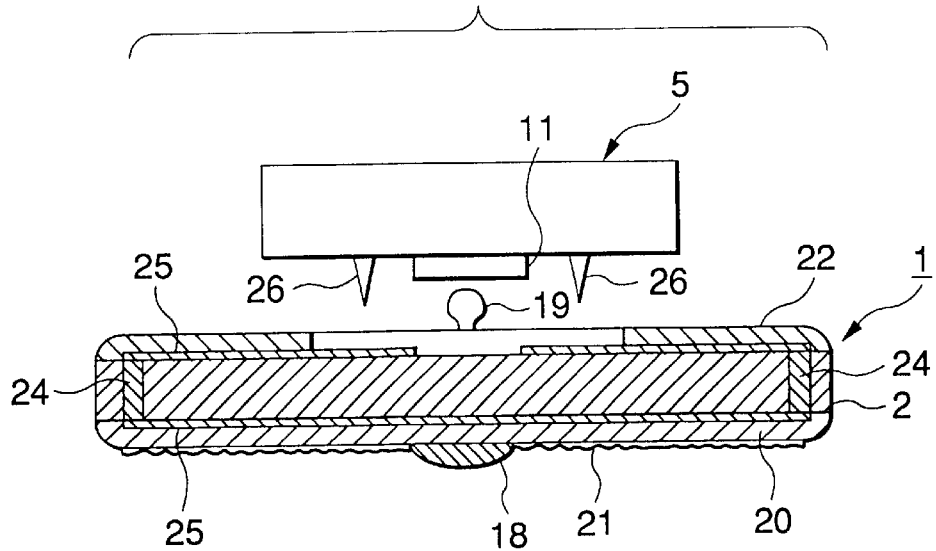
FIG. 13 is a longitudinal sectional view to show a configuration example of a third embodiment of the invention.

FIG. 13 is a longitudinal sectional view to show a configuration example of a third embodiment of the invention. Parts identical with or similar to those previously described with reference to FIG. 1 to FIG. 4 are denoted by the same reference numerals in FIG. 13 and will not be discussed again in detail. The third embodiment is characterized by the fact that a part of a loop antenna 3 is formed according to a thin film technology of silk print, etc. As shown in FIG. 13, through holes are made near two opposed sides of a support 2 and are filled with conductive material 24. The support 2 is formed on both faces with conductive thin films 25 according to the thin film technology and the upper conductive thin film 25 is divided into two portions. The upper and lower conductive thin films 25 are electrically connected at both ends to the conductive material 24 with which the through holes are filled, forming the loop antenna 3.

The upper and lower faces of the support 2 are covered with insulating sheets 20 and 22 for covering the conductive thin films 25 and the upper insulating sheet 22 is cut at the center for exposing the conductive thin film 25 at both ends thereof. When a transmitter 5 is placed on a living body placement section 1, a pair of conductive contact connectors 26 projecting from the lower face of the transmitter 5 abuts the exposure parts of the conductive thin film 25 at both ends thereof for introducing a signal transmitted from the transmitter 5 into the loop antenna formed of the conductive thin films 25. A hook 19 fixed to an electrode 4 is coupled to a connector 11 like a concave hook to the transmitter 5, as in the first embodiment.

According to the third embodiment, the manufacturing process is simplified and costs can be reduced as compared with the case where the loop antenna 3 is formed as a thin-film separate body and is folded at both ends back to the support 2 and fixed as in the configuration examples of the first and second embodiments.

In FIG. 13, an embodiment configured to include one electrode 4 is shown, but the third embodiment can also be applied to the case where the number of the electrodes 4 is two or more as in the configuration example of the embodiment shown in FIG. 9 and FIG. 10 and the embodiment where the electrode 4 is the transducer 23 as shown in FIG. 12; similar advantages can be provided.

Fourth Embodiment

Figure 14:
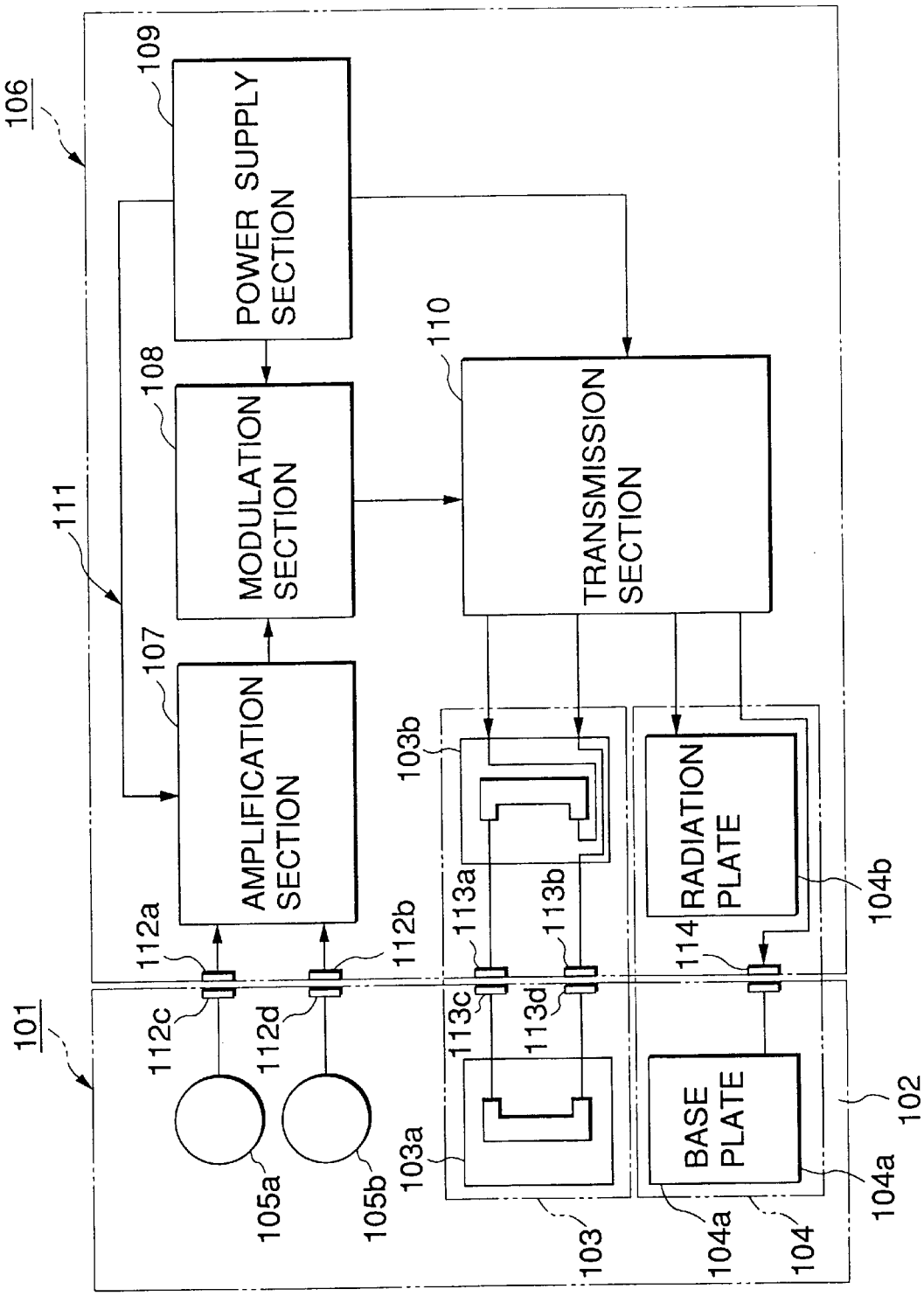
FIG. 14 is a block diagram to show the configuration of a fourth embodiment of a biological signal transmission apparatus of the invention.
Figure 15:
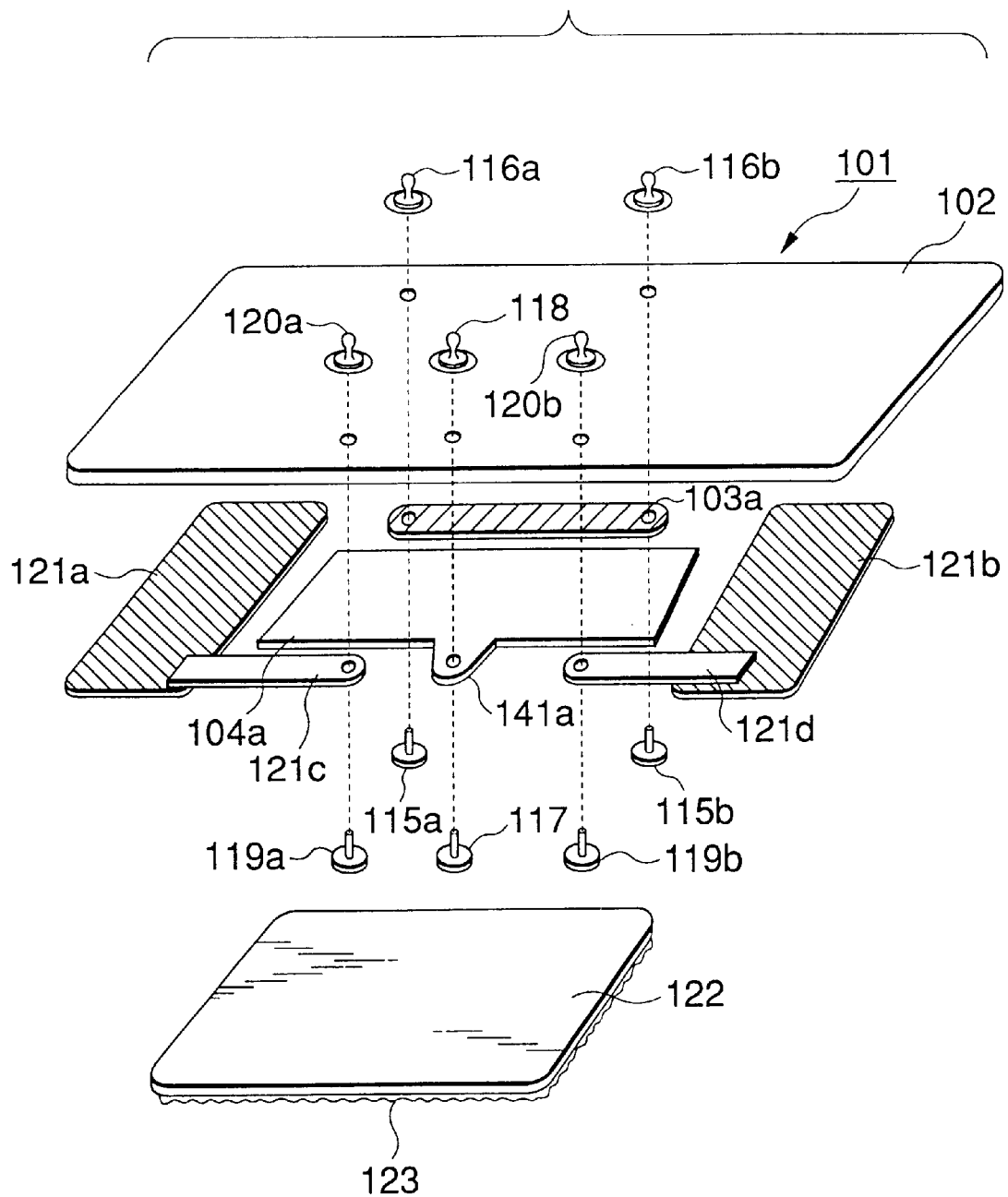
FIG. 15 is an exploded perspective view to show a configuration example of a living body placement section in FIG. 14.
Figure 16:
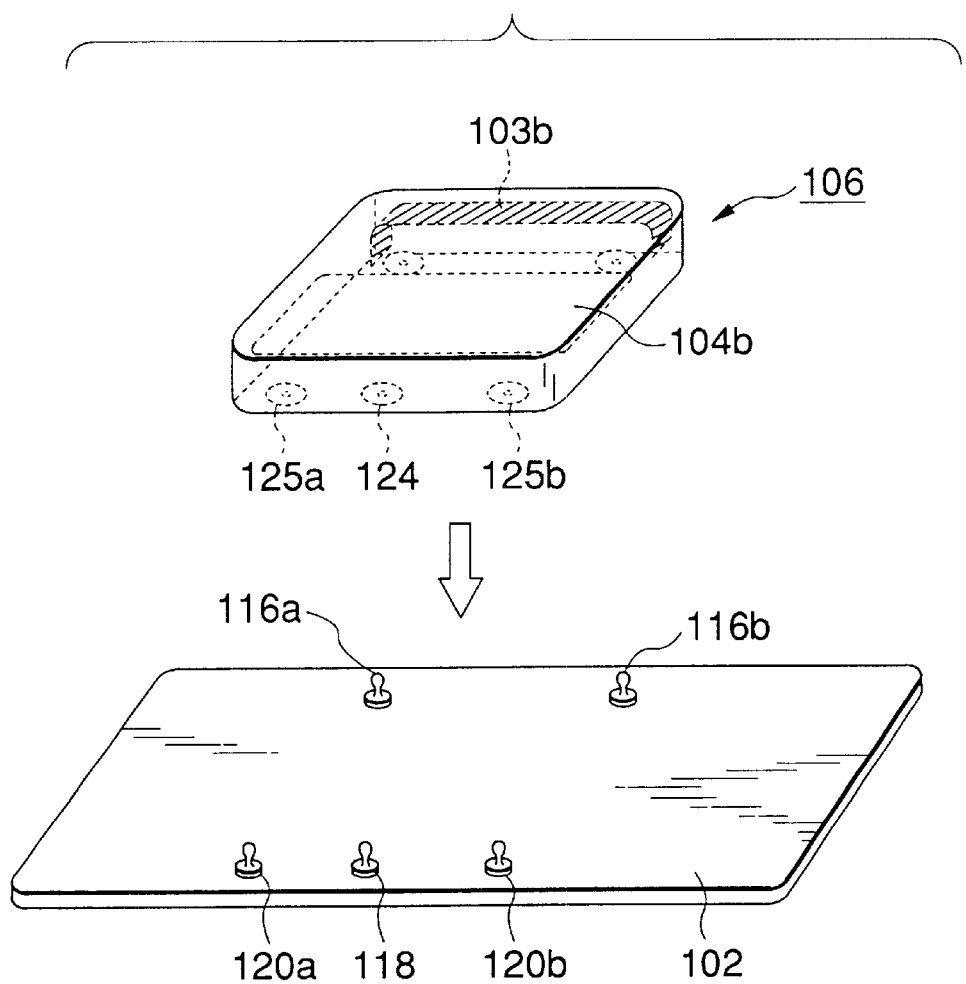
FIG. 16 is an external perspective view of the living body placement section shown in FIG. 15 and a transmitter placed thereon.
Figure 17:
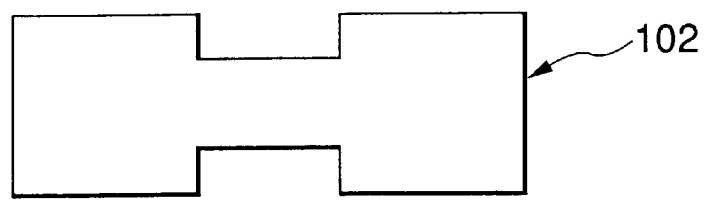
FIG. 17 is a plan view to show the form of a modified example of a support in FIG. 15.
Figure 18:
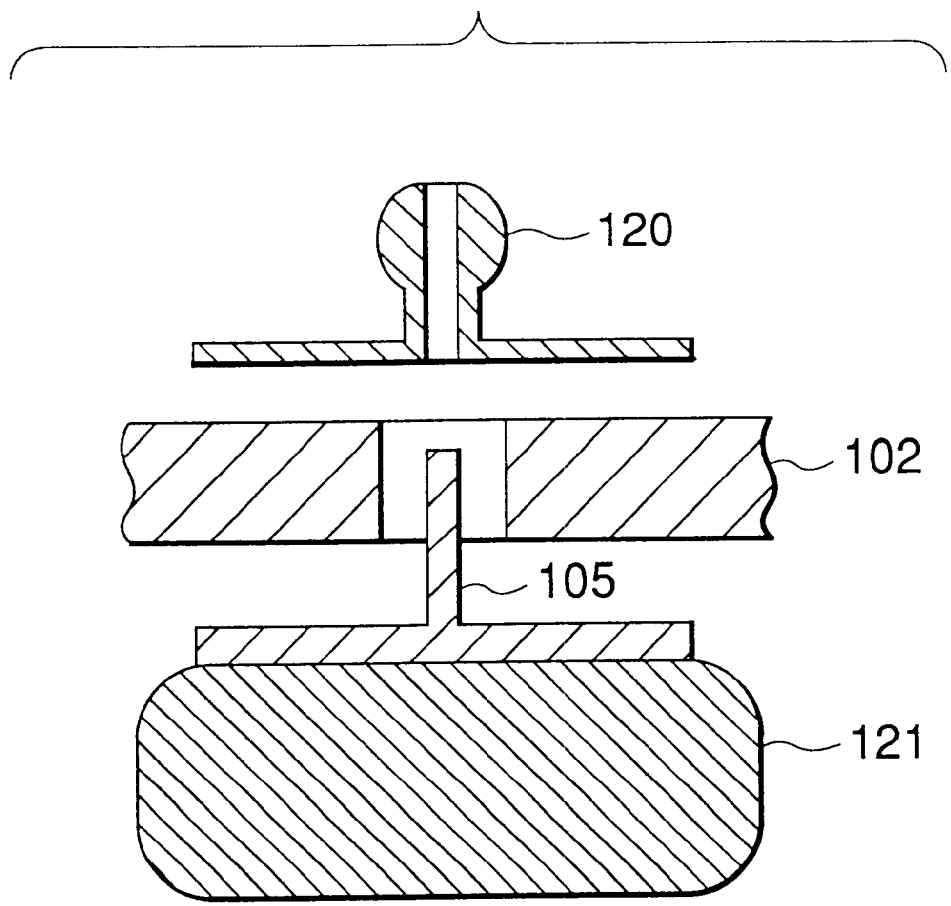
FIG. 18 is an exploded longitudinal sectional view to show the attachment structure of an electrode in FIG. 17.

FIG. 14 is a block diagram to show a configuration example of a fourth embodiment of the invention. FIG. 15 is an exploded perspective view to show a specific configuration example of a living body placement section in FIG. 14. FIG. 16 is an external perspective view of the living body placement section shown in FIG. 14 and a transmitter placed thereon. FIG. 17 is a plan view to show the form of a modified example of a support in FIG. 15. FIG. 18 is a drawing to show the attachment structure of an electrode in FIG. 17.

In FIG. 14, a living body placement section 101 comprises division parts 103a and 104a of two antennas 103 and 104 each divided into two parts and two electrodes 105a and 105b mounted on a flat support 102 formed of an insulating material. In the embodiment, the antenna 103 is a loop antenna and the antenna 104 is a microstrip antenna (MSA). A transmitter 106 comprises electric circuitry 111 made up of an amplification section 107, a modulation section 108, a power supply section 109, and a transmission section 110 and other division parts 103b and 104b of the two antennas 103 and 104. The electrodes 105a and 105b and the amplification section 107 are connected through connectors 112a and 112b, one end of the part 103a of the antenna 103 and one end of the part 103b of the antenna 103 are connected through a connector 113a, and the opposite end of the part 103a of the antenna 103 and the transmission section 110 are connected through a connector 113b. The opposite end of the part 103b of the antenna 103 is connected to the transmission section 110. The part 104a of the antenna 104 (MSA) is a base plate and the part 104b of the antenna 104 is a radiation plate. The base plate 104a is connected to the transmission section 110 through a connector 114 and the radiation plate 104b is directly connected to the transmission section 110.

Power is supplied from the power supply section 109 to the amplification section 107, the modulation section 108, and the transmission section 110. When the support 102 is placed on the living body surface of a subject, biological signals detected on the electrodes 105a and 105b are amplified by the amplification section 107 and are modulated by the modulation section 108, then are sent from the transmission section 110 to the antennas 103 and 104. The biological signals are transmitted by radio from the antennas 103 and 104 to a receiver (not shown).

In FIG. 15 and FIG. 16, the support 102 is formed of a dielectric material like a rectangular plate. The loop antenna 103 formed of a conductive material like a belt is divided into two parts. One loop antenna part 103a is placed on one side of the lower face of the support 102 and caulking devices 115a and 115b are inserted into both ends of the loop antenna part 103a. The caulking devices 115a and 115b pass through the loop antenna part 103a from the lower face thereof and further pass through the support 102 and project upward. Hooks 116a and 116b are fixed to the projection ends of the caulking devices 115a and 115b by caulking. The loop antenna part 103b is connected at one end to the hook 116a. The hook 116b is connected to the transmission section 110.

As described above, the MSA 104 consists of the base plate 104a and the radiation plate 104b, which are opposed to each other in parallel. As shown in FIG. 15, the base plate 104a is fixed almost at the center of the lower face of the support 102 and is formed with a projection 141a at the center of one side opposite to the loop antenna part 103a. A caulking device 117 is inserted into the projection 141a; it passes through the base plate 114a from the lower face thereof and further passes through the support 102 and projects upward. A hook 118 for the base plate is fixed to the projection ends of the caulking device 117 by caulking.

A pair of plate-like conductive terminals 121c and 121d is placed at both sides of the projection 141a of the base plate 104a in parallel with one side of the base plate 104a and are fixed to the lower face of the support 102. Caulking devices 119a and 119b are inserted into opposed ends of the conductive terminals 121c and 121d; they pass through the conductive terminals 121c and 121d from the lower faces thereof and further pass through the support 102 and project upward. Hooks 120a and 120b for deriving electrocardiographic signals are fixed to the projection ends of the caulking devices 119a and 119b by caulking. Conductive water-containing gels 121a and 121b are attached to outer ends of the conductive terminals 121c and 121d. Further, the lower faces of the loop antenna part 103a, the base plate 104a, and the conductive terminals 121c and 121d are covered with an insulating sheet 122 and an adhesive 123 is applied to the lower face of the insulating sheet 122.

The transmitter 106 is shaped like a square can as shown in FIG. 16 and contains a board (not shown) on which the electric circuitry 111 is mounted. On the board, the loop antenna part 103b and the radiation plate 104b are placed at the positions corresponding to the loop antenna part 103a and the base plate 104a in the living body placement section 101, as shown in FIG. 15. When the transmitter 106 is attached to the living body placement section 101, the hook 116a projecting from the top of the support 102 of the living body placement section 101 is fitted to one end of the loop antenna part 103b and the convex hooks 118, 120a, and 120b are connected to concave hooks 124, 125a, and 125b formed at predetermined positions of the board. The concave hooks 124, 125a, and 125b are connected to the electric circuitry 111. Further, the opposite end of the loop antenna part 103b is also connected to the electric circuitry 111.

Next, specific structures and materials of the parts of the fourth embodiment shown in FIG. 14 to FIG. 18 will be discussed in detail. The support 102 is formed of a dielectric substance which is several ten μm to several mm thick, for example, and has reasonable rigidity and dielectric constant for holding the living body placement section 101. In the above-described example, the support 102 is shaped like a rectangular plate, but may be of any shape like a hand drum, for example, as shown in FIG. 17. The support 102 may be formed of a material of a dielectric substance having a dielectric constant fitted to the use frequency and the shapes of the base plate 104a and the radiation plate 104b, for example, paper or a macromolecular dielectric substance, such as vinyl chloride, polyurethane, polystyrene, polycarbonate, polypropylene, fluoroplastics, silicone resin, cellulose acetate, polyester, rayon, nylon, vinylon, epoxy resin, or ceramics.

The loop antenna 103 is several μm to several mm thick, for example, has a surrounding length of about several times the wavelength to about several the tenths of the wave length, and is formed of an elongated conductive film. The planar shape is not limited. For example, metal, carbon, a macromolecular conductive substance, or resin to which conductive plating is given is used as the material of the loop antenna 103.

The base plate 104a basically has a large area in the allowable range and a structure for making a signal emitted from the radiation plate 104b hard to be affected by a human body, etc. For example, metal, carbon, a macromolecular conductive substance, or resin to which conductive plating is given is used as the material of the base plate 104a. The shape of the base plate 104a also changes corresponding to the antenna characteristics.

The radiation plate 104b is formed of a conductive film which is several μm to several mm thick, for example, and has an area determined by frequency. In the above-described example, the radiation plate 104b is shaped like a rectangular plate, but may be of any shape. For example, metal, carbon, a macromolecular conductive substance, or resin to which conductive plating is given is used as the material of the radiation plate 104b like the base plate 104a.

The caulking devices 115a, 115b, 117, 119a, and 119b and the conductive terminals 121c and 121d are fixed to the support 102 through the hooks 116a, 116b, 118, 120a, and 120b, are conductive substances themselves, and act as electrodes for deriving a living body electricity phenomenon and electrodes for transferring signals to the base plate 104a. They may be of any structure if it can be stably fixed to the hook 120 as the connector, for example, as shown in FIG. 18. The material may be a conductive substance and is not limited. For example, a macromolecular conductive substance, such as conductive rubber or water-containing resin, metal, such as copper, stainless steel, or aluminum, carbon, such as carbon fibers or graphite, resin to which conductive plating is given (for example, a conductive metal film of gold, silver, copper, nickel, aluminum, palladium, platinum, etc., is formed on the surface of a macromolecular insulating substance or a macromolecular conductive substance by means of sputtering evaporation, electrolytic plating, electroless plating, etc.,) is used as the material.

In the above-described example, the hooks 116a, 116b, 118, 120a, and 120b are used as the parts forming the connectors 112c, 112d, 113c, 113d, and 114, but the scope of the invention is not limited to them. For example, a structure of a general-purpose electric connector, a contact-type connector, etc., may be used. A material similar to that of the caulking devices 115a, 115b, 117, 119a and 119b described above can be used.

The water-containing gel 121a, 121b makes electric conduction between the conductive terminal 121c, 121d and a living body surface and preferably it has adhesion to a living body. For example, gelatin, polyacrylic acid, its salt, karaya gum, any other water-soluble or water-dispersable acrylic-family polymer, polyacrylic-family polymer, water-soluble or water-dispersable polymer of polyacrylamide, polyvinyl alcohol, carboxymethyl cellulose, polyurethane, etc., or the like can be named as the base material for forming the gel layer. The length and breadth of the water-containing gels 121a, 121b to be attached to living body is the range from approximately 2 to 6 cm. But the shape of the water-containing gels are not limited as described shape, and any figure like a square, rectangle, circle, oval are applicable.

Preferably, the distance between nearest of water-containing gels 121a, 121b is the range from approximately 1.0 to 7.5 cm to detect heat rate information and etc. And more specifically, it's preferable to make the distance approximately 2.0 to 7.5 cm to detect a small amplitude P wave of ECG sufficiently.

The insulating sheet 122 is provided so that a human body and the radiation plate 104b and the base plate 104a making up the antenna do not come in direct contact with each other. It may be made of any material if the material has an insulating property; the material is not limited.

The adhesive 123 is provided for strongly fixing the living body placement section 101 to a living body; preferably it is a substance not giving an impetus to the living body. For example, a known adhesive material excellent in intimate contact with the living body placement section 101, such as double-sided adhesive tape, an acrylic family, a rubber family, a silicone family, or a vinyl ether family, can be used.

The transmitter 106 is attached to the living body placement section 101 as described above, whereby the loop antenna parts 103a and 103b are connected, forming one loop antenna 103, and the base plate 104a and the radiation plate 104b are connected through the circuit on the board, forming the MSA 104. When the described biological signal transmission apparatus is placed on a living body surface as shown in FIG. 30, the living body placement section 101 is bonded to the surface of the living body of a subject via the adhesive 123 and the water-containing gels 121a and 121b are attached at a first intercostal space left sternal border on a left chest along a position 800b in such a manner that the water-containing gels 121a and 121b are positioned through midclavicular line and are parallel to a clavicle, as shown in FIG. 38. Thus, there is obtained biological signals 801b which is highly corrective to ECG detected in the method of standard limb lead (II). In addition, the stable ECG having high correction with ECG of standard limb lead (II) can be obtained as ling as the living body placement section is attached to area within the range of 2.5 cm apart from the 800b, or second intercostal space and it's not always needed to position water-containing gels 121a and 121b through midclavicular line.

Upon the attachment, as shown in FIG. 39, the water-containing gels 121a and 121b are attached on a chest defiend between a xiphoid process and a navel through and perpendicular to a midsternal line so as to obtain biological signals 801a which is highly correlative to ECG detected in the method of standard limb lead (II).

In addition, the stable ECG having high correlation to ECG of standard limb lead (II) can be obtained as long as the living body placement section is attached to area within the range of 2.5 cm apart from the 800a, and it's not always needed to position water-containing gels 121a and 121b through midsternal line.

Biological signals detected on the conductive terminals 121c and 121d are sent through the hooks 120a and 120b to the transmitter 106 and are processed by the electric circuitry 111 in the transmitter 106, then are sent through the hooks 116a and 116b to the loop antenna 103 and through the hook 118 to the MSA 104 from which the biological signals are transmitted to the receiver (not shown) by radio.

According to the embodiment, the biological signals detected on the electrodes 105a and 105b are transmitted by radio through the loop antenna 103 and the MSA 104 different in characteristics, so that the directivity can be improved, the radiation capability can be enhanced, and the radio wave band width can be enlarged. The loop antenna 103 and the MSA 104 are each divided into two parts, one of which is placed in the support 102 and the other in the transmitter 106. Thus, the transmitter 106 can be miniaturized as compared with the case where the whole antennas are installed in the transmitter 106.

Figure 19:
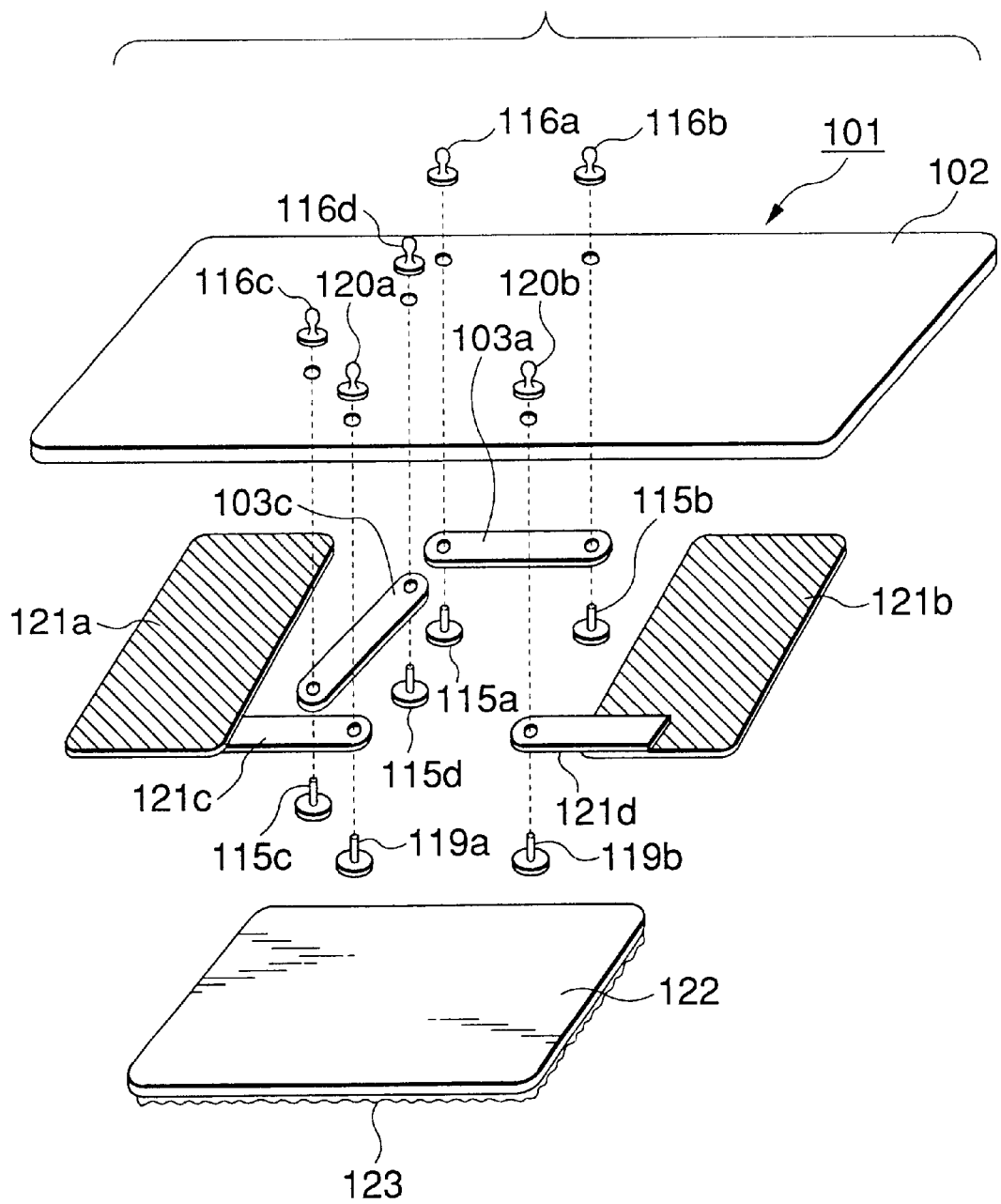
FIG. 19 is an external perspective view to show another configuration example of the living body placement section in FIG. 14.
Figure 20:
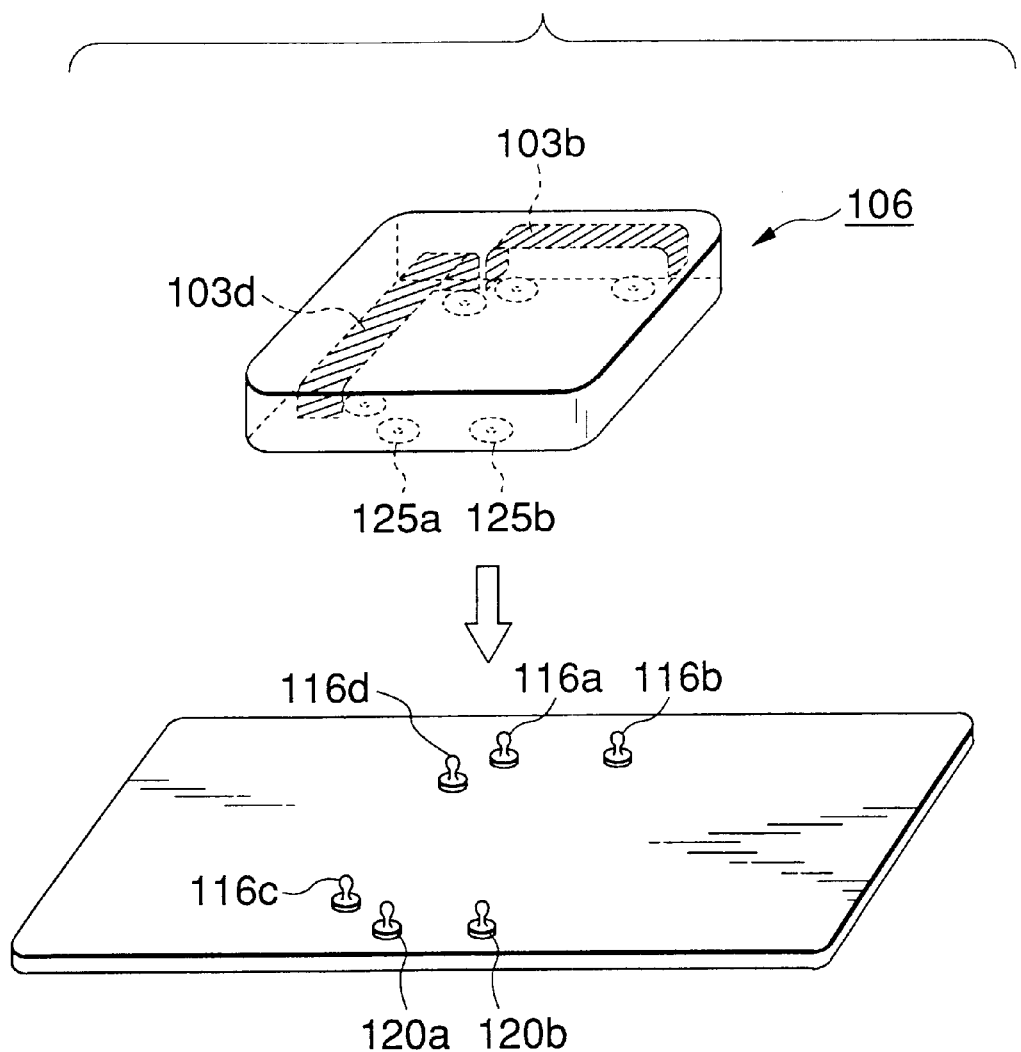
FIG. 20 is an external perspective view of the living body placement section shown in FIG. 19 and a transmitter placed thereon.

In the embodiment, the two electrodes 105 are used, but similar functions and advantages can be provided if one electrode 105 is used. Two loop antennas 103 each divided into two parts (103a and 103b and 103c and 103d) may be provided in place of the MSA 104, as shown in FIG. 19 and FIG. 20. In this case, the 103a and 103c are placed in a direction orthogonal to each other and the 103b and 103d are placed in a direction orthogonal to each other, whereby the directivity can be improved. In this case, the hooks 116a and 116c are connected to ends of the loop antenna parts 103b and 103c and the hooks 116d and 116b are connected to the transmission section 110 of the electric circuitry 111. Opposite ends of the loop antenna parts 103b and 103c are connected to the transmission section 110 of the electric circuitry 111.

Fifth Embodiment

Figure 23:
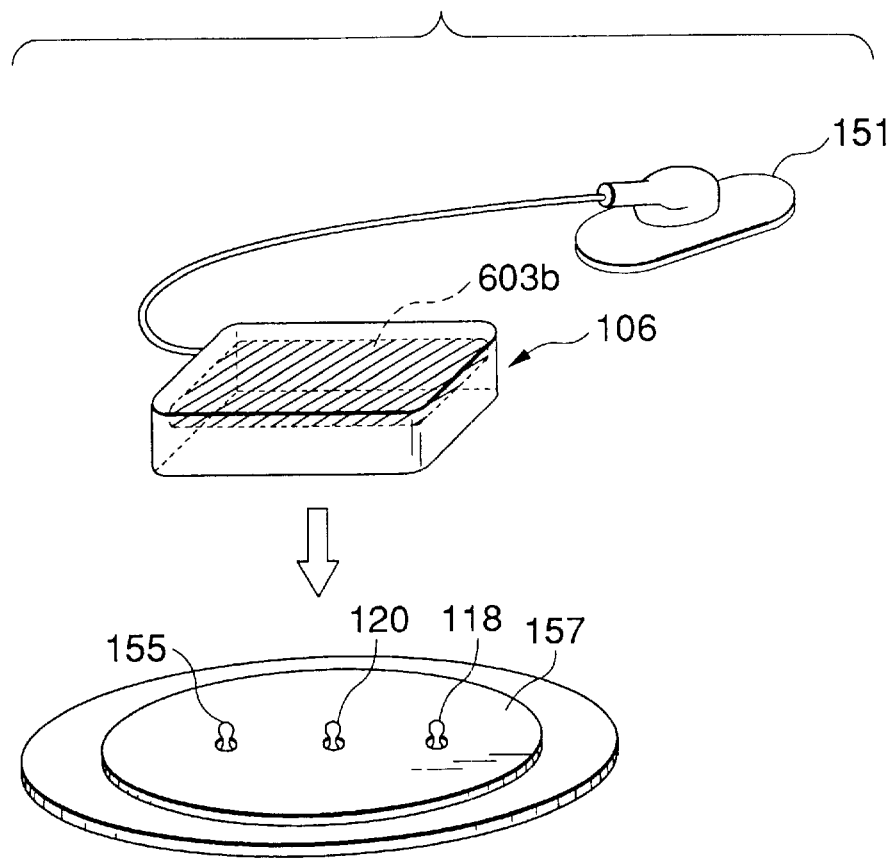
FIG. 23 is an external perspective view of the living body placement section shown in FIG. 22 and a transmitter placed thereon.
Figure 24:
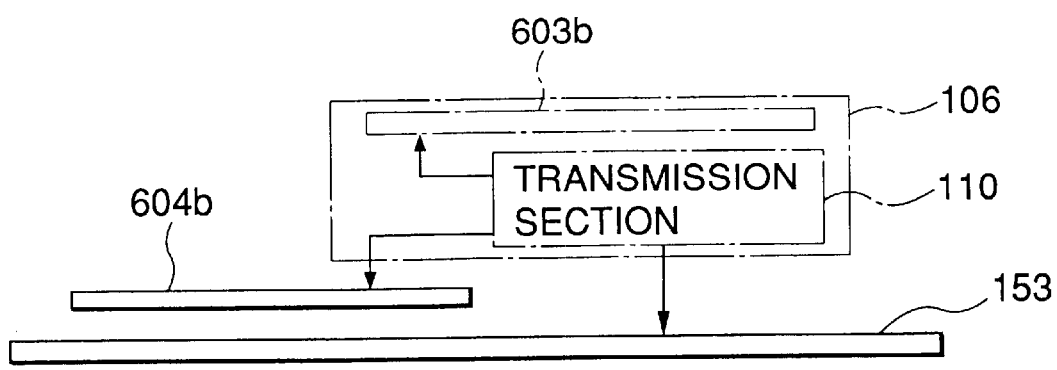
FIG. 24 is a schematic representation to show placement of antennas when the transmitter in FIG. 23 is placed on the living body placement section.
Figure 25:
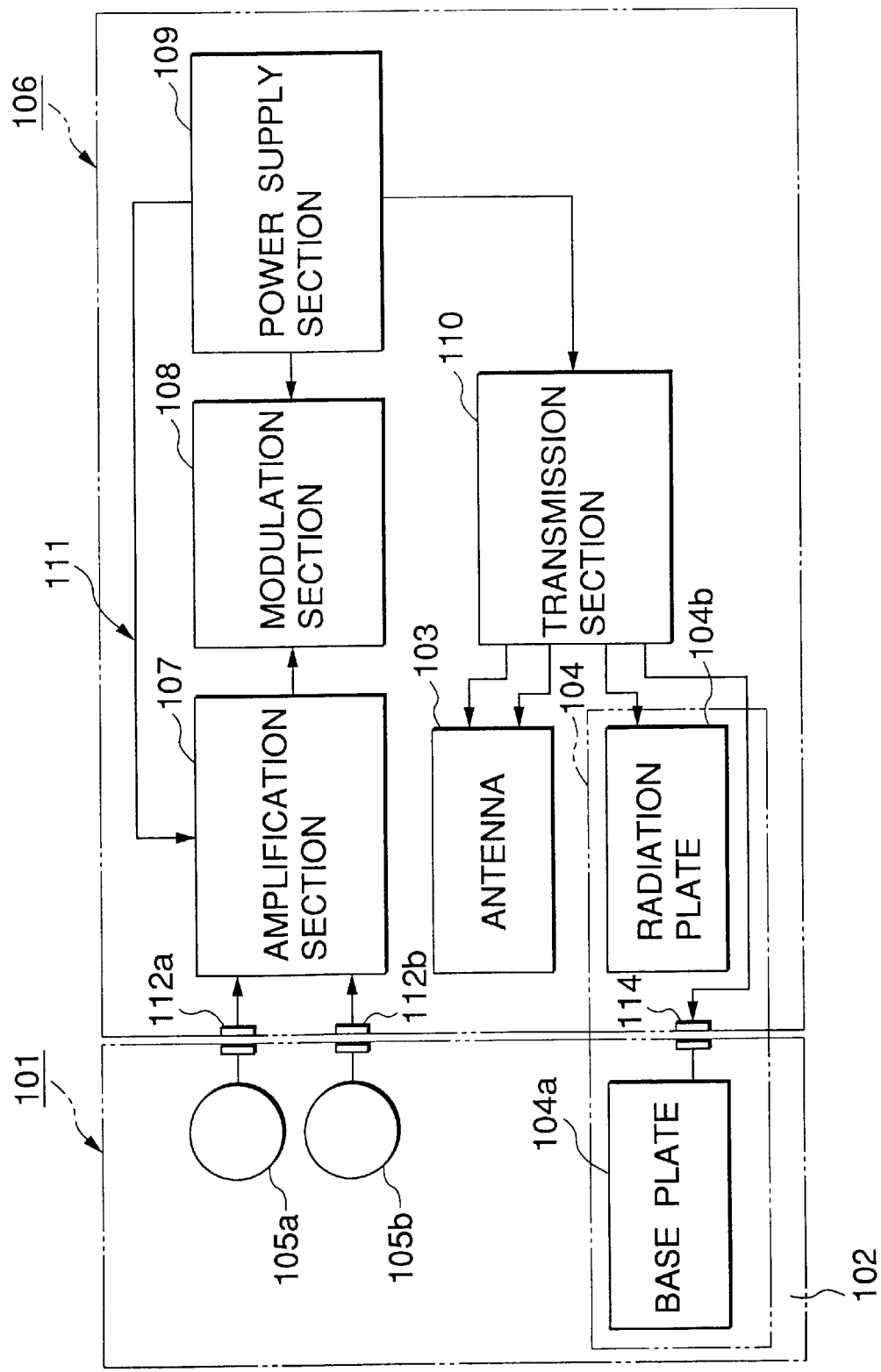
FIG. 25 is a block diagram to show a configuration example of a sixth embodiment of the invention.
Figure 26:
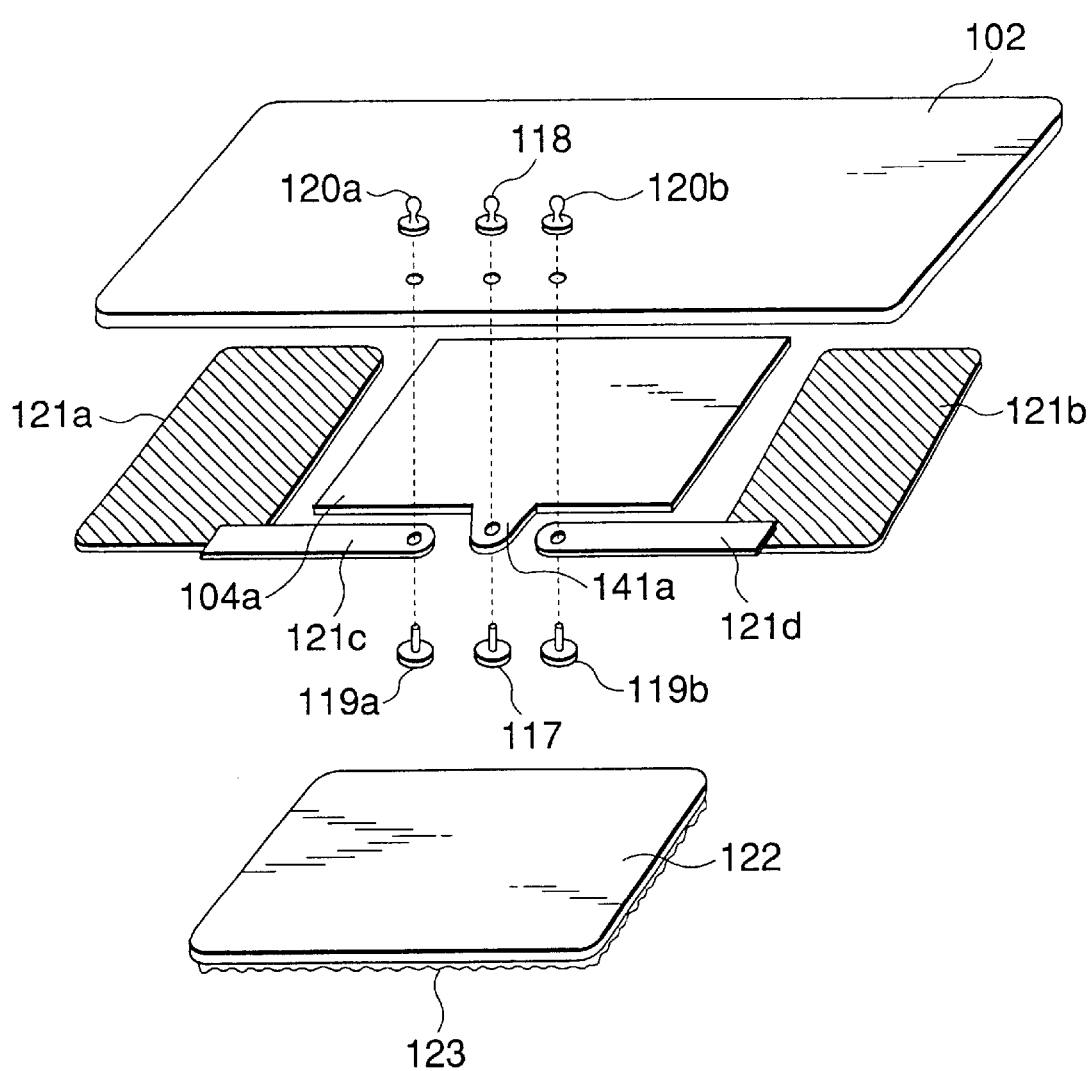
FIG. 26 is an exploded perspective view to show a configuration example of a living body placement section in FIG. 25.
Figure 27:
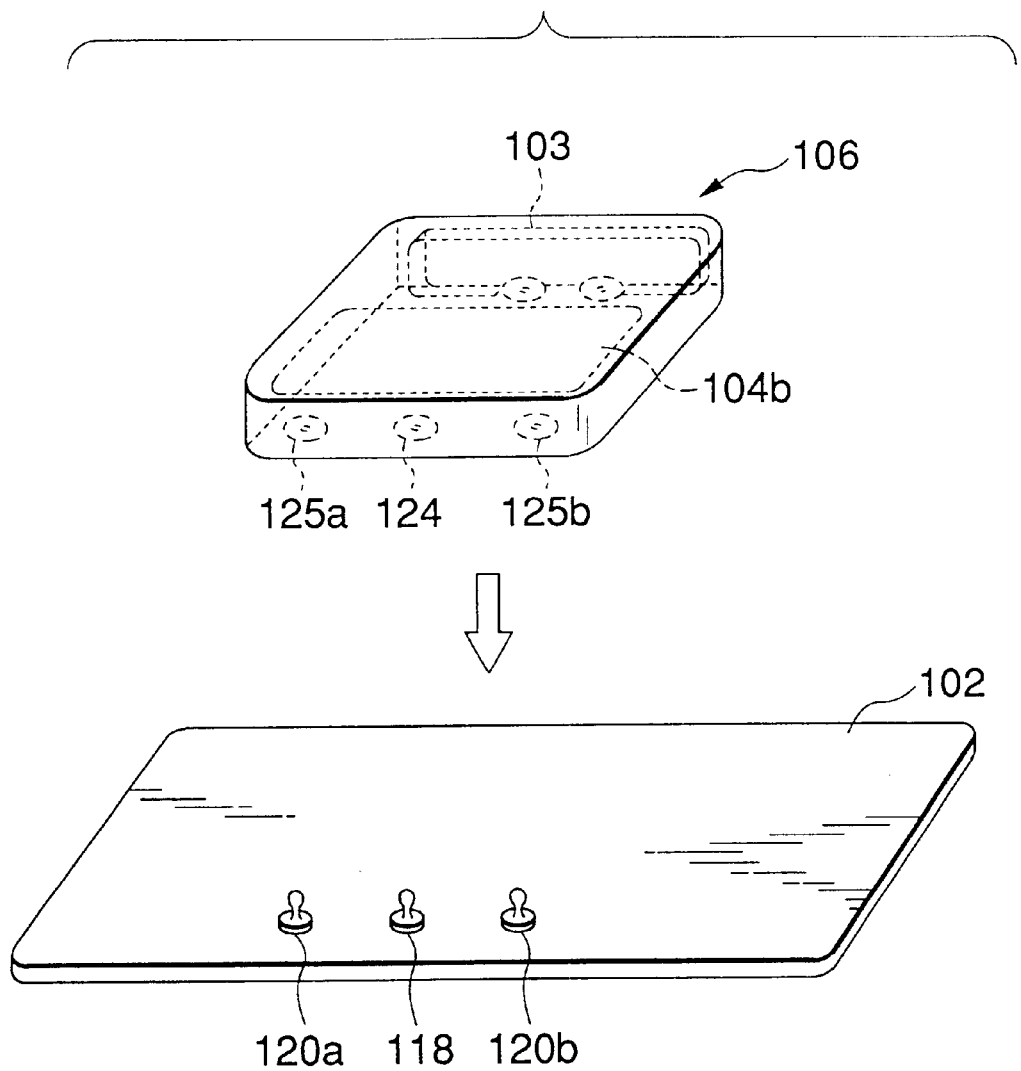
FIG. 27 is an external perspective view of the living body placement section shown in FIG. 26 and a transmitter placed thereon.

FIG. 21 to FIG. 24 show a configuration example of a fifth embodiment of the invention and FIG. 25 to FIG. 27 show a configuration example of a sixth embodiment of the invention. Parts identical with or similar to those previously described with reference to FIG. 14 to FIG. 16 are denoted by the same reference numerals in FIG. 21 to FIG. 27 and will not be discussed again in detail.

Figure 21:
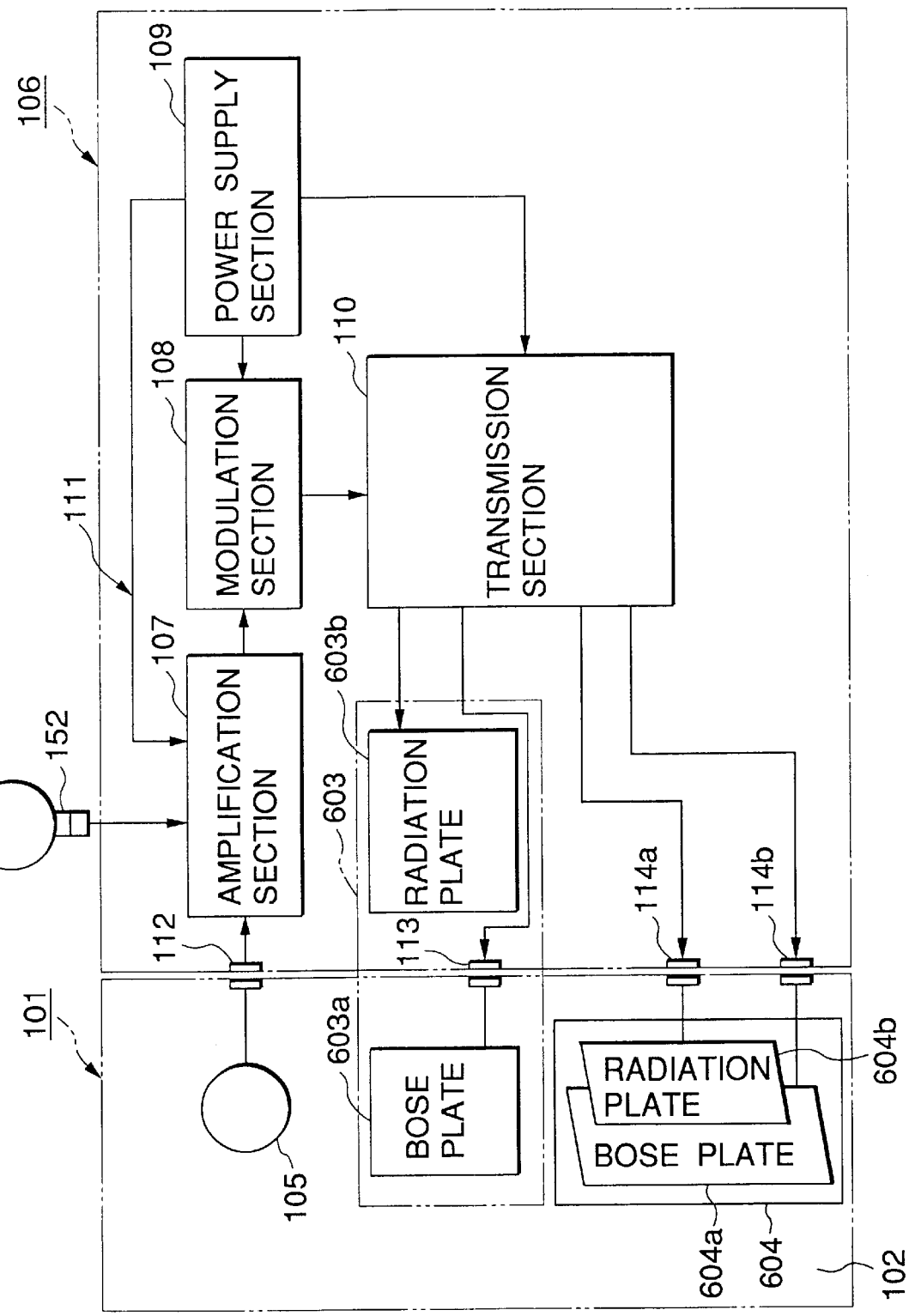
FIG. 21 is a block diagram to show a configuration example of a fifth embodiment of the invention.
Figure 22:
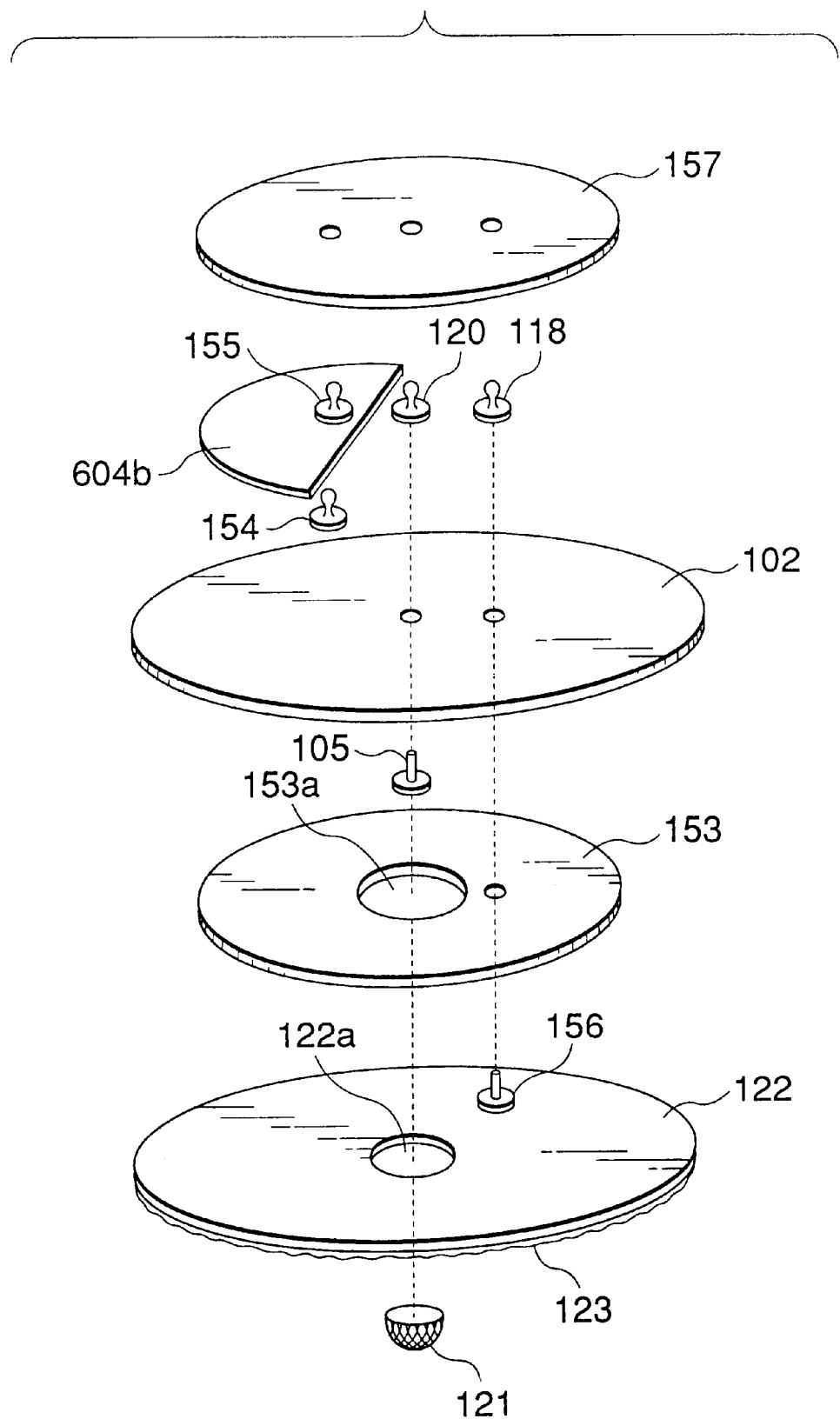
FIG. 22 is an exploded perspective view to show a configuration example of a living body placement section in FIG. 21.

FIG. 21 is a block diagram to show a configuration example of the fifth embodiment of the invention. FIG. 22 is an exploded perspective view to show a specific configuration example of a living body placement section in FIG. 21. FIG. 23 is an external perspective view of the living body placement section shown in FIG. 22 and a transmitter placed thereon. FIG. 24 is a schematic representation to show placement of antennas when the transmitter in FIG. 23 is placed on the living body placement section.

The embodiment is characterized by the fact that one antenna 603 of two antennas 603 and 604 is divided into two parts, that one antenna division part 603a, an electrode 105, and the whole antenna 604 are placed on a support 102, and that the other antenna division part 603b is placed in a transmitter 106, as shown in FIG. 21. In the embodiment, one electrode 105 is used and a connector 151 placed on another part of a living body is connected to an amplification section 107 through a connector 152, but two or more electrodes 105 may be used. In the embodiment, the antennas 603 and 604 are MSAs, one antenna 603 is divided into two parts, and only the radiation plate 603b of the divided antenna 603 is placed in the transmitter 106.

In FIG. 22, a radiation plate 604b like a semi-disk is fixed to the upper face of the support 102 formed of a dielectric material like a disk and a base plate 153 like a disk is fixed to the lower face of the support 102 concentrically. A caulking device 154 is inserted into the radiation plate 604b of the MSA 604 from the lower face thereof and a hook 155 for the radiation plate is fixed to the upper end of the caulking device 154 projecting from the radiation plate 604b by caulking.

A caulking device 156 is inserted into the base plate 153 from the lower face thereof and passes through the support 102 and projects upward. A hook 118 for the ground plate is fixed to the projection end by the caulking. The electrode 105 is inserted into the center of the support 102 from the lower face thereof and passes through the support 102 and projects upward. A hook 120 for deriving an electrocardiographic signal is fixed to the projection end by the caulking. Further, conductive water-containing gel 121 is attached to the lower end of the electrode 105.

The upper face of the support 102 is covered with a disk-like insulating sheet 157 and the hooks 118, 120, and 155 pass through the insulating sheet 157 and project upward. Likewise, the lower face of the support 102 is covered with a disk-like insulating sheet 122 and the electrode 105 and the water-containing gel 121 pass through openings 153a and 122a made in the centers of the base plate 153 and the insulating sheet 122 and project downward.

On the other hand, the radiation plate 603b is placed in the transmitter 106. When the transmitter 106 is placed on the support 102 through the hooks 118, 120, and 155, the radiation plate 603b is opposed to the base plate 153 placed on the support 102, forming one MSA 603. Since the radiation plate 604b and the base plate 153 are opposed to each other on the support 102, another MSA 604 is formed on the support 102. The two MSAs 603 and 604 share the base plate 153, as shown in FIG. 24.

According to the embodiment, functions and advantages almost similar to those of the fourth embodiment can be provided. In the fifth embodiment, one electrode 105 is installed in a living body placement section 101, but if two electrodes 105 are installed, they are placed in a similar manner to that shown in FIG. 15.

Sixth Embodiment

FIG. 25 is a block diagram to show a configuration example of the sixth embodiment of the invention. FIG. 26 is an exploded perspective view to show a specific configuration example of a living body placement section in FIG. 26. FIG. 27 is an external perspective view of the living body placement section shown in FIG. 26 and a transmitter placed thereon.

The embodiment basically has almost the same configuration as the fifth embodiment except that an antenna 103 not divided into two parts is placed in a transmitter 106 as shown in FIG. 25 or that two electrodes 105 are provided. The number of the electrodes 105 may be one.

In FIG. 26 and FIG. 27, the antenna 103 is a loop antenna, an antenna 104 is an MSA, the loop antenna 103 is placed in the transmitter 106, and a base plate 104a and a radiation plate 104b of the MSA 104 are placed in a living body placement section 101 and the transmitter 106 respectively. The attachment structure of the base plate 104a, the electrodes 105, and an insulating plate 122 is similar to that in the fourth embodiment shown in FIG. 15. When the transmitter 106 is placed on the living body placement section 101, the base plate 104a and the radiation plate 104b are opposed to each other, forming the MSA 104.

According to the embodiment, functions and advantages almost similar to those of the fourth embodiment can be provided. In the sixth embodiment, the number of the electrodes 105 is two, but if one electrode 105 is used, it is placed in a similar manner to that shown in FIG. 22.

Seventh Embodiment

Figure 28:
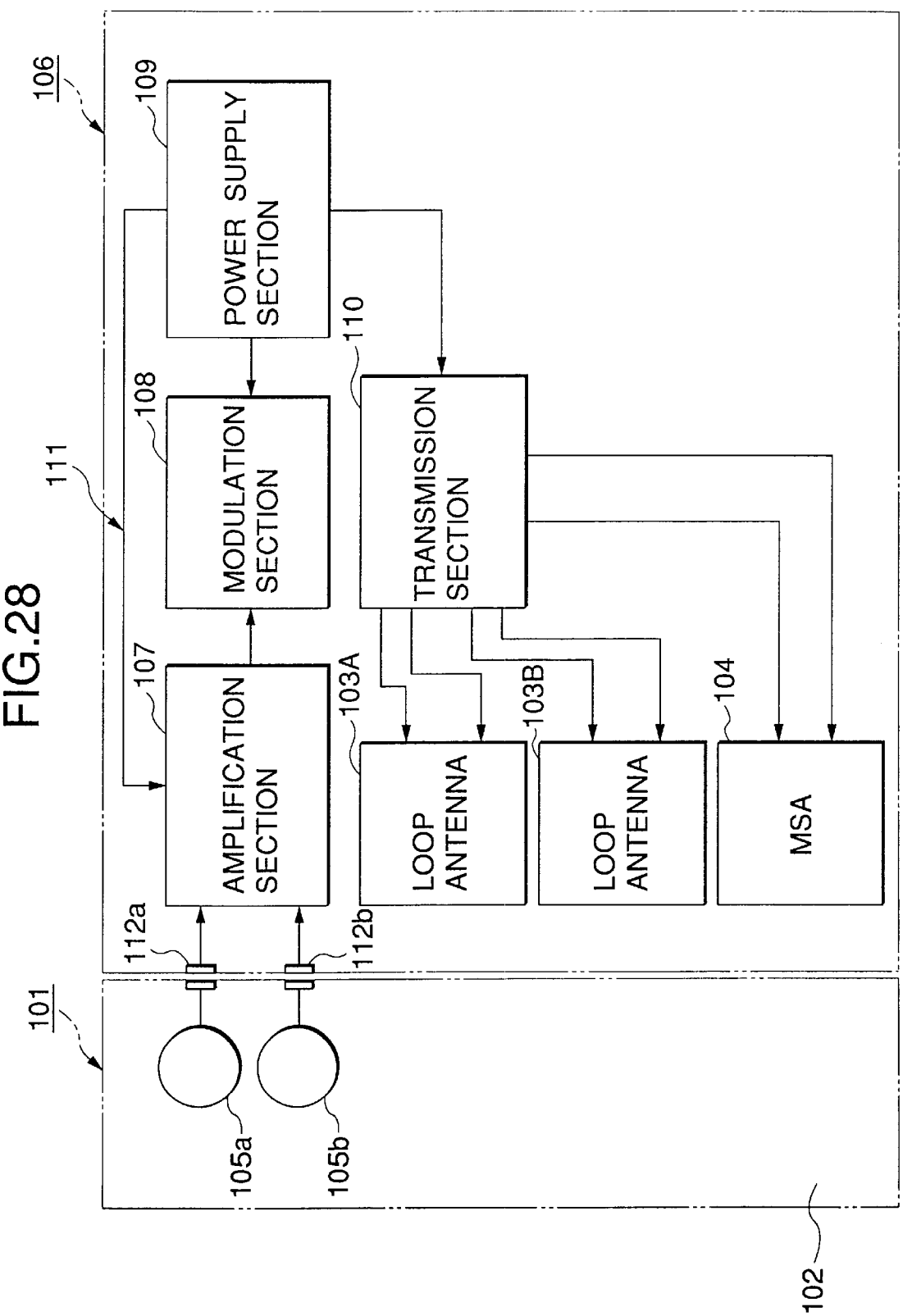
FIG. 28 is a block diagram to show a configuration example of a seventh embodiment of the invention.
Figure 29:
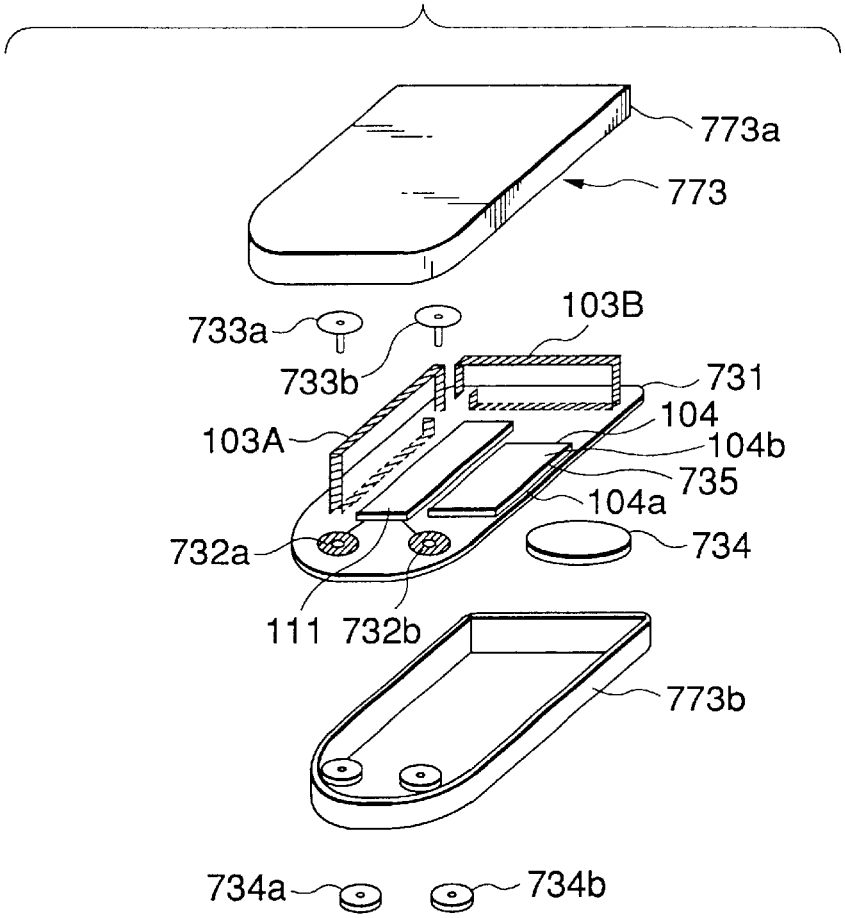
FIG. 29 is an exploded perspective view to show a configuration example of a living body placement section and a transmitter in FIG. 28.

A seventh embodiment of the invention will be discussed. FIG. 28 is a block diagram to show a configuration example of the seventh embodiment of the invention. FIG. 29 is an exploded perspective view. In the embodiment, two loop antennas 103A and 103B and an MSA 104 are attached to a transmitter 106.

As shown in FIG. 28, a living body placement section 101 comprises a pair of electrodes 105a and 105b integrally mounted on a support 102. The transmitter 5 contains electric circuitry 111 made up of an amplification section 107, a modulation section 108, a power supply section 109, and a transmission section 110. The loop antennas 103A and 103B and the MSA 104 are electrically connected to the electric circuitry 111. The amplification section 107 and the electrodes 105 are connected electrically and mechanically through connectors 112.

Power is supplied from the power supply section 109 to the amplification section 107, the modulation section 108, and the transmission section 110. When the support 102 is placed on the living body surface of a subject, biological signals detected on the electrodes 105a and 105b are amplified by the amplification section 107 and are modulated by the modulation section 108, then are sent from the transmission section 109 to the loop antennas 103A and 103B and the MSA 104. The biological signals are transmitted by radio from the antennas 103A, 103B, and 104 to a receiver (not shown).

As shown in FIG. 29, a board 731 is housed in a cabinet 773 consisting of an upper lid 773a and a lower lid 773b. The two loop antennas 103A and 103B are installed so that their loop opening faces are orthogonal to the board face of the board 731 and are orthogonal to each other. The two loop antennas 103A and 103B are placed in the proximity of the margins of the board 731 and are connected to the electric circuitry 111.

The board 731 is provided with lands 732a and 732b for guiding biological signals detected from water-containing gels 718a and 718b and transferred through conductive terminals 718c and 718d, caulking devices 731a and 731b, and convex hooks 719a and 719b into the electric circuitry 111. The board 731 is fixed to the lower lid 773b in parallel with the bottom face thereof by means of caulking devices 733a and 733b inserted into holes made in the centers of the lands 732a and 732b and holes made in projections of the inside of the lower lid 773b from above and concave hooks 734a and 734b corresponding to the caulking devices 733a and 733b. When the apparatus is placed on a living body, the bottom face of the lower lid 773b becomes almost parallel with the living body surface, so that the opening faces of the two loop antennas 103A and 103B become almost orthogonal to the living body surface.

Further, the MSA 104 consisting of a radiation plate 104b and a base plate 104a placed in parallel on a dielectric support member 735 is installed on the board 731. As described above, the board 731 is fixed to the lower lid 773b in parallel with the bottom face thereof. Thus, when the apparatus is placed on a living body, the radiation plate 104b and the base plate 104a become almost parallel with the living body surface. At this time, the base plate 104a is nearer to the lower lid 773b side than the radiation plate 104b is, and thus is nearer to the living body surface than the radiation plate 104b is.

A battery storage section is provided in the rear face of the board 731 and a battery 734 is stored in the battery storage section.

The support 102 is formed of an insulating material like a plate and is narrow at the center. Projections of the caulking devices 731a and 731b are inserted into the holes made in ends of the conductive terminals 718c and 718d placed on the lower face of the support 102 and are fixed to the support 102 together with the conductive terminals 718c and 718d by means of the convex hooks 719a and 719b. The conductive water-containing gels 718a and 718b are attached to the opposite ends of the conductive terminals 718c and 718d. Insulating sheets 720a and 720b are attached to the bottom faces of the caulking devices 731a and 731b for electrically insulating from a living body.

The structures and materials of the members in the embodiment are almost similar to those of the corresponding members used with the above-described embodiments.

According to the embodiment, the two loop antennas 103A and 103B, which are orthogonal to each other, are excellent in directivity, and since the opening faces of the loop antennas 103A and 103B are orthogonal to the living body surface, the sensitivity improves and the gain can be increased. In addition, all the antennas 103A, 103B, and 104 are contained in the transmitter, thus the living body placement section 101 can be removed from the transmitter 106 so that only the living body placement section 101 can be made disposable; costs for use can be reduced.

Figure 31A:
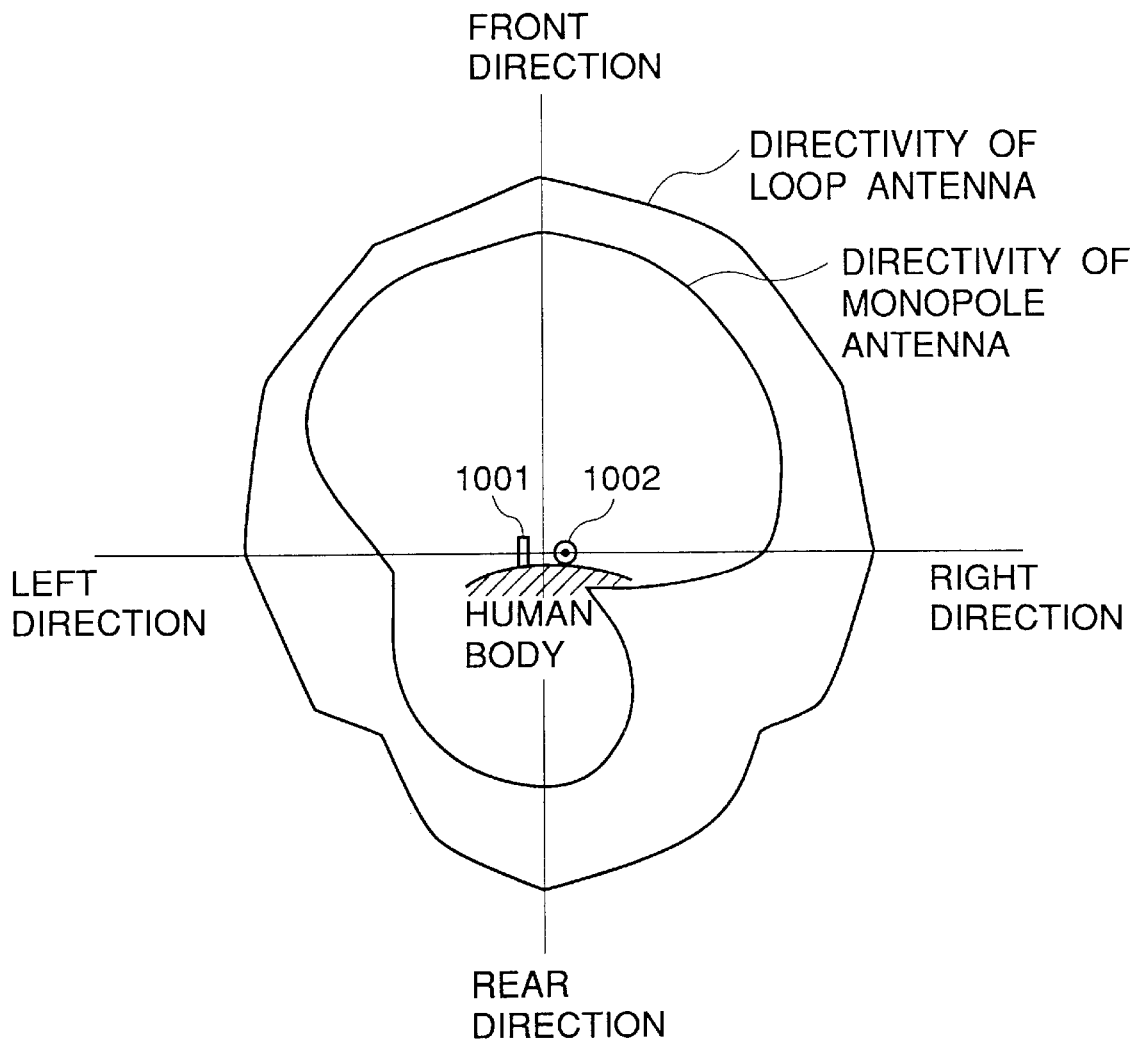
FIG. 31(a) is a plan view of an illustration to compare a loop antenna and a monopole antenna placed on a human body in directivity and FIG. 31(b) is side view of the arrangement of the loop antenna and the monopole antenna attached with the human body along with FIG. 31(a)
Figure 31B:
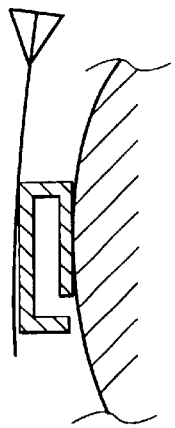
Figure 32A:
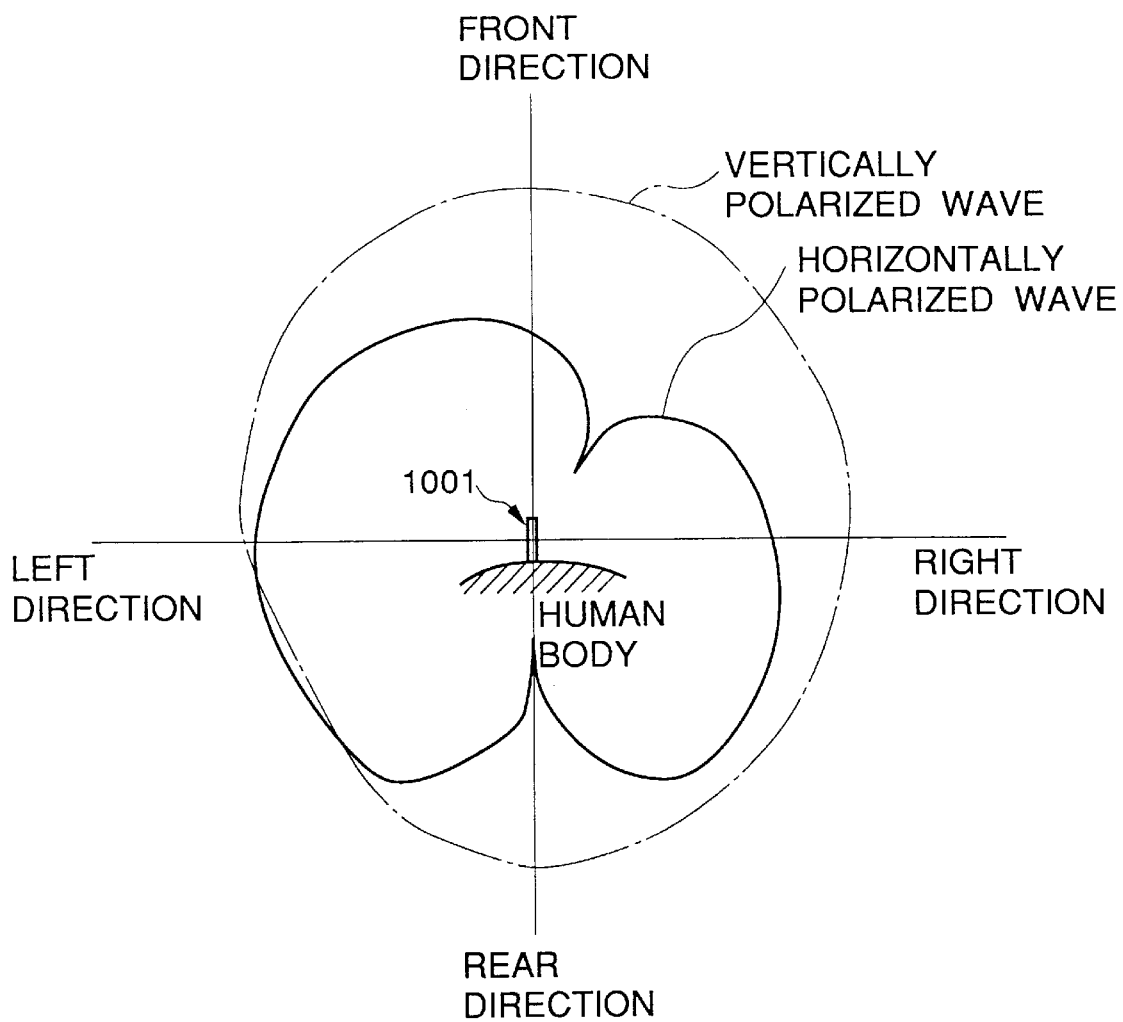
FIG. 32(a) is a plan view of an illustration to show the directivity of one loop antenna placed on a human body.
Figure 32B:
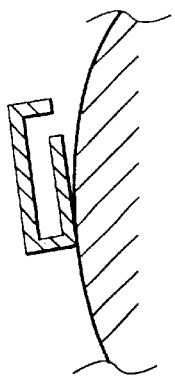
FIG. 32(b) is side view of the arrangement of one loop antenna attached with the human body along with FIG. 32(a)
Figure 33A:
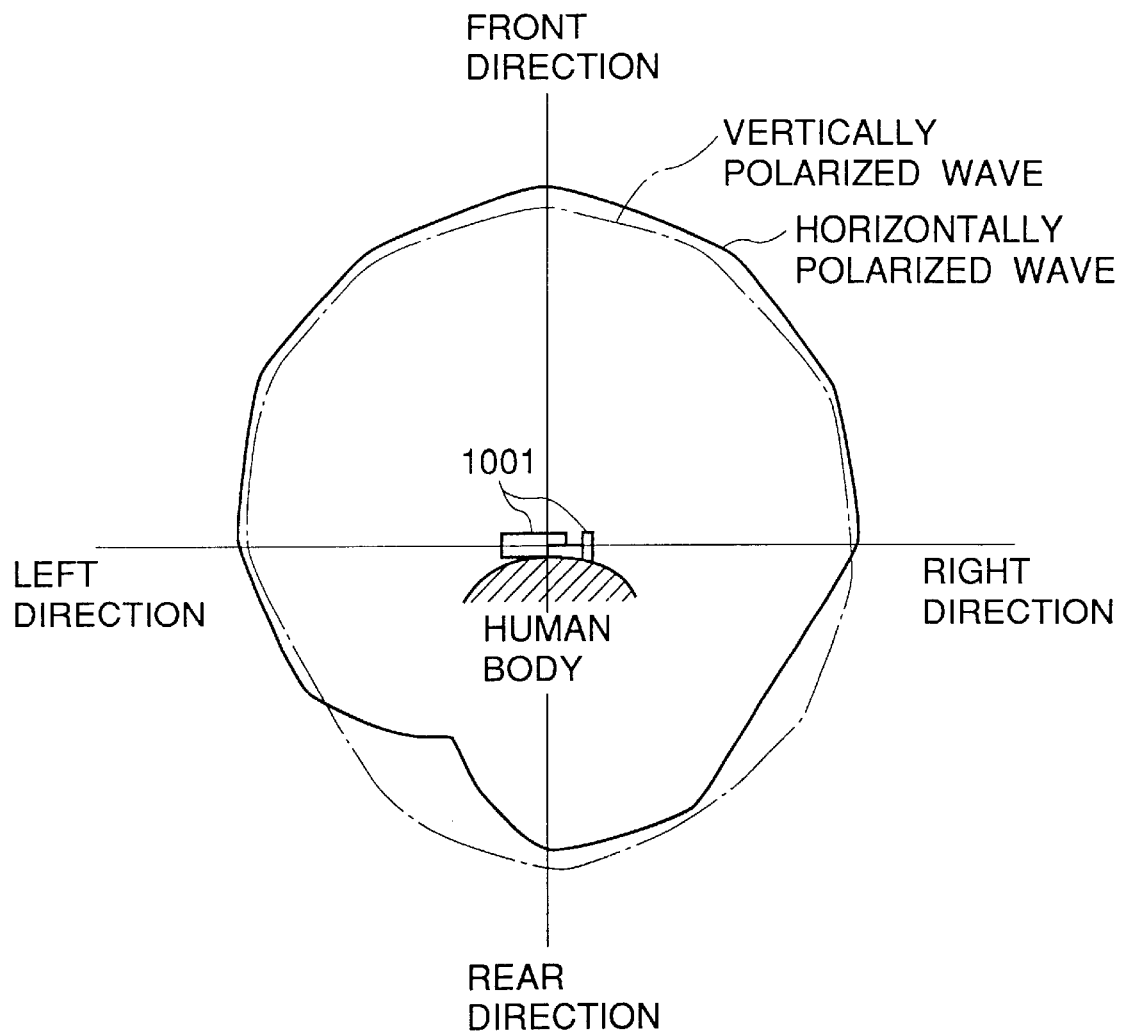
FIG. 33(a) is a plan view of an illustration to show the directivity of two loop antennas placed on a human body.
Figure 33B:
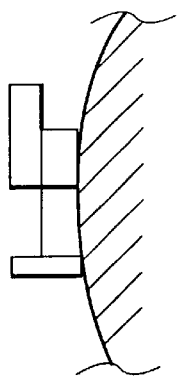
FIG. 33(b) is side view of the arrangement of two loop antennas attached with the human body along with FIG. 33(a)
Figure 34:
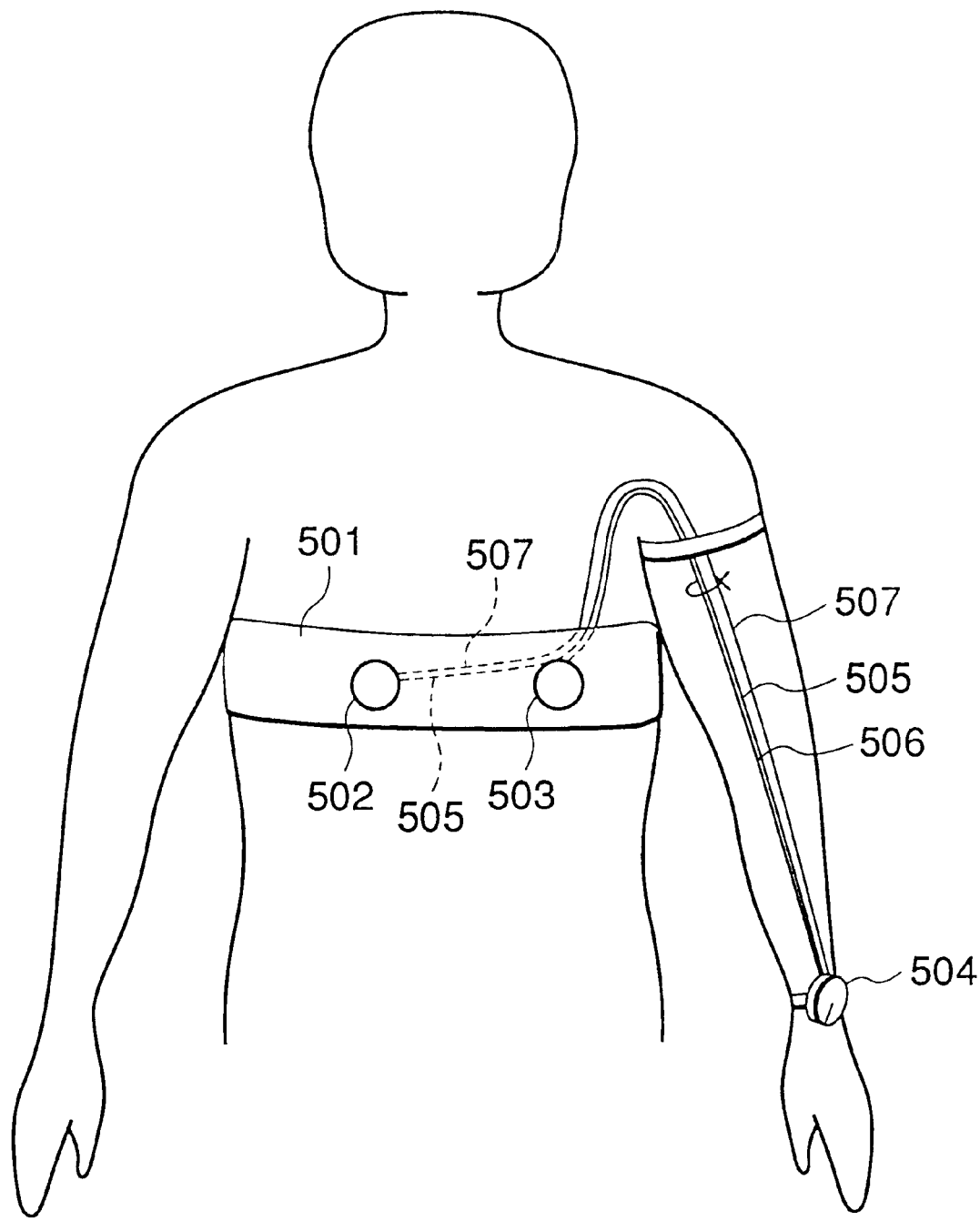
FIG. 34 is a front view to show the configuration of a first example of a biological signal transmission apparatus in a related art.
Figure 35:
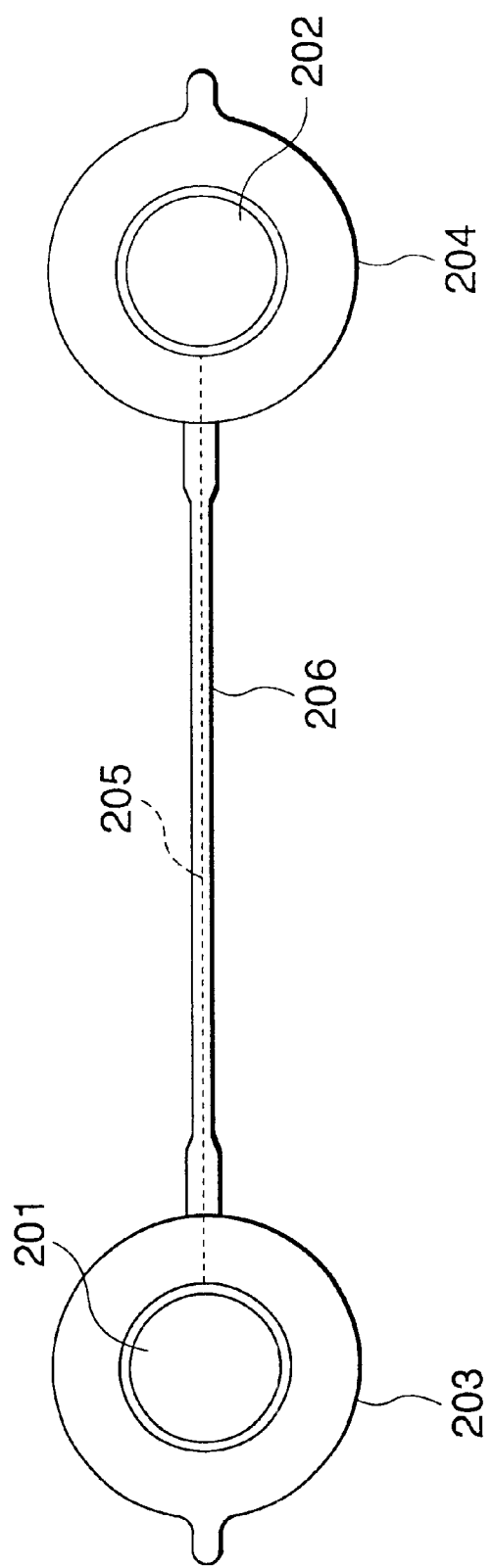
FIG. 35 is a plan view to show the configuration of a second example of a biological signal transmission apparatus in a related art.
Figure 36:
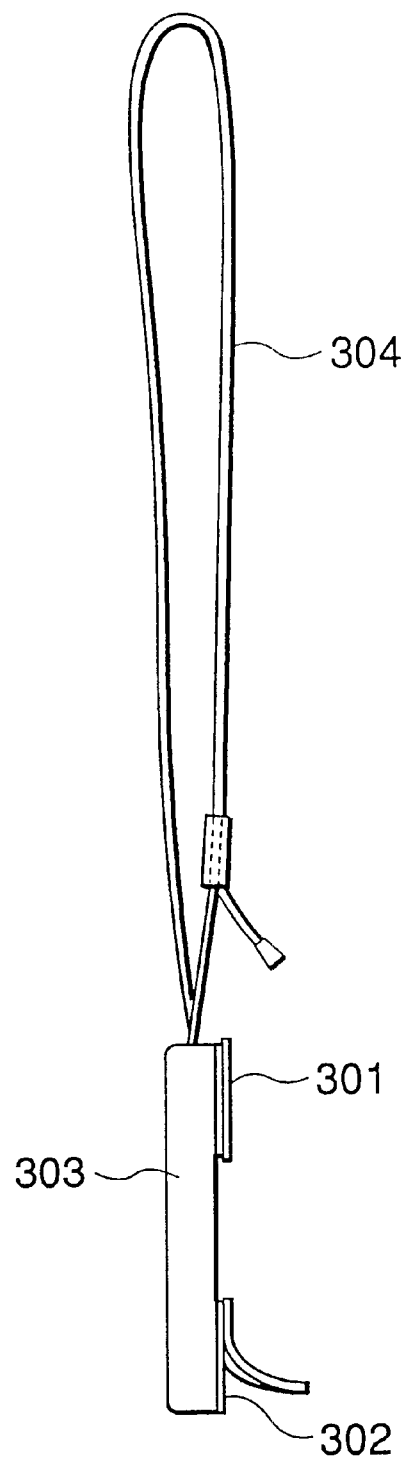
FIG. 36 is a front view to show the configuration of a third example of a biological signal transmission apparatus in a related art.
Figure 37:
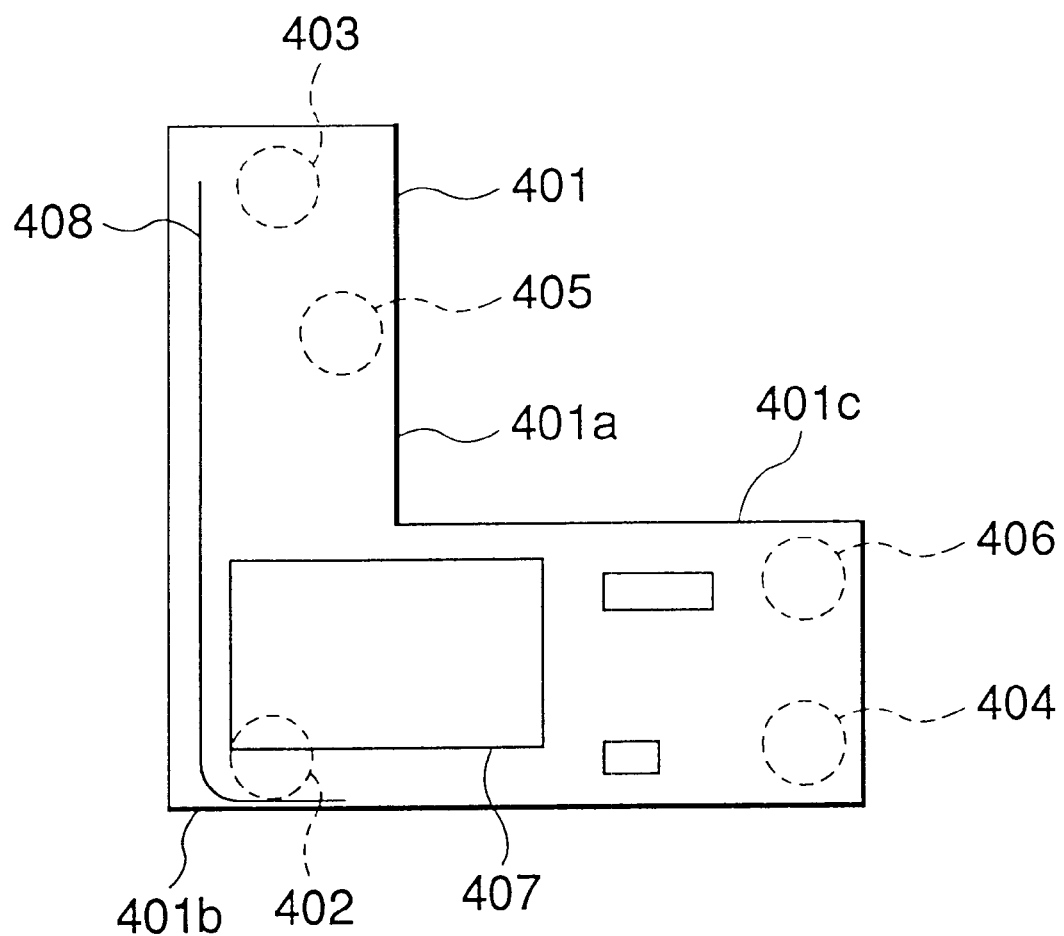
FIG. 37 is a plan view to show the configuration of a fourth example of a biological signal transmission apparatus in a related art.

FIG. 31(a) shows radio wave directivity of a loop antenna 1001 and a monopole antenna 1002, affected by a human body. As shown here, when the opening face of the loop antenna is placed at right angles to the surface of a human body, remarkably excellent directivity is provided as compared with the case where the monopole antenna is placed in roughly parallel with the surface of the human body. FIG. 31(b) is side view of the arrangement of the loop antenna and the monopole antenna attached with the human body along with FIG. 31(a). FIG. 32(a) is an illustration to show directivity provided when the opening face of one loop antenna 1001 is placed at right angles to the surface of a human body. FIG. 32(b) is side view of the arrangement of one loop antenna attached with the human body along with FIG. 32(a). FIG. 33(a) is an illustration to show directivity provided when the opening faces of two loop antennas 1001 are placed at right angles to the surface of a human body and are orthogonal to each other. FIG. 33(b) is side view of the arrangement of two loop antennas attached with the human body along with FIG. 33(a). As shown here, if two loop antennas 1001 are provided, they make a complement to each other in directivity and are less affected by the human body.

According to the biological signal transmission apparatus of the present invention, when the apparatus is placed on a living body, it can be placed so that the loop opening face of the loop antenna becomes almost at right angles to the living body surface. Thus, the loop opening face can hold a constant direction relative to the living body surface and the human body, etc., does not block the opening face, so that attenuation of radio waves because of the effect of the human body can be lessened, the gain can be improved, and stable directivity can be provided.

According to the biological signal transmission apparatus of another embodiment, when the apparatus is placed on a living body, the loop opening faces of the two loop antennas become almost at right angles to the living body surface and are placed in a direction almost perpendicular to each other. Thus, the loop antennas make a complement to each other in directivity and the gain can be improved.

According to the biological signal transmission apparatus of a further embodiment at least one loop antenna is contained in the transmitter, thus the person on whom the apparatus is placed is not restrained as compared with an antenna placed on the outside such as a monopole antenna ($\lambda/4$ antenna). The manufacturing cost of the support supporting the electrode and placed on the living body surface can be reduced and can be made disposable.

According to the biological signal transmission apparatus of another embodiment, at least one of the loop antennas is divided into two parts, one loop antenna division part is placed in the support and the other is placed in the transmitter, and the transmitter is placed on the support, thereby putting the loop antenna division parts into one piece. Thus, the transmitter can be miniaturized or the loop opening face can be enlarged as compared with the case where all loop antennas are installed in the transmitter. Since the loop antenna is closely fixed in the proximity of a living body with the opening face orthogonal to the living body surface, the gain is also improved.

According to the biological signal transmission apparatus of the present invention, the loop antenna for emitting a biological signal is integral with the support supporting the electrode, on which the transmitter is placed, and when the support is placed on the living body surface, the opening face of the loop antenna becomes almost at right angles to the living body surface, thus attenuation of radio waves of the loop antenna can be lessened and the gain can be improved.

According to a further embodiment of the biological signal transmission apparatus of the present invention, the loop antenna disposed so that the opening face is placed in a direction almost perpendicular to the living body surface, and the microstrip antenna having a radiation plate and a base plate opposed in parallel with the living body surface, the base plate being placed nearer to the living body surface, are placed, so that attenuation of radio waves because of the effect of the human body can be lessened and the two antennas make a complement to each other in directivity, thus the gain can be improved.

According to a further embodiment of the biological signal transmission apparatus of the present invention, two loop antennas are disposed so that the opening faces are placed in a direction almost perpendicular to the living body surface and are almost at right angles to each other, and a microstrip antenna having a radiation plate and a base plate opposed in parallel with the living body surface, the base plate being placed nearer to the living body surface, are provided, so that the three antennas make a complement to each other in directivity and the gain can be improved.

According to yet a further embodiment of the biological signal transmission apparatus of the present invention, at least one of the loop antennas and the microstrip antenna is contained in the transmitter, so that the person on whom the apparatus is placed is not restrained as compared with a monopole antenna, etc., placed on the outside. Further, the manufacturing cost of the support supporting the electrode and placed on the living body surface can be reduced.

According to another embodiment of the present invention, the loop antenna or the microstrip antenna can be placed on the support occupying a larger area than the transmitter, so that the loop opening area of the loop antenna can be enlarged and the areas of the radiation plate and the base plate of the microstrip antenna can be made large. Thus, the gain and band width can be improved.

According to another embodiment the present invention, the microstrip antenna having a radiation plate and a base plate opposed in parallel with the living body surface, the base plate being placed nearer to the living body surface, is provided, so that the microstrip antenna placed in parallel with the living body surface can be thinned and a large projection such as a monopole antenna is removed from the living body surface. Since the base plate is placed between the radiation plate and the living body surface, the antenna performance is less affected by the living body.

According to another embodiment of the present invention, the microstrip antenna is contained in the transmitter, whereby the patient is not restrained as compared with an antenna placed on the outside such as a monopole antenna. Further, the manufacturing cost of the support supporting the electrode and placed on the living body surface can be reduced.

According to yet a further embodiment of the present invention, the microstrip antenna is integral with the support and is connected to output of the electric circuitry through a connection member and the transmitter is placed on the support. Thus, the radiation plate and the base plate can be placed on the support occupying a larger area than the transmitter, so that they can be formed largely and the gain and band width can be improved.

According to positioning of biological signal transmission apparatus of the present invention, ECG wave which is highly correlative to ECG detected in the method of standard limb lead (II) can be obtained by positioning two electrodes in the vicinity of first and second intercostal space left sternal border parallel to clavicle on a left chest or at area defined between a xiphoid process and a navel perpendicular to a midsternal line on a chest that help diagnosis of ECG wave easily.

What is claimed is:

1. A method of detecting a ECG wave of a subject, comprising:
    (a) positioning two electrodes within 2.5 cm of an area defined by a first or second intercostal space sternal border parallel to a clavicle;
    (b) detecting a ECG wave from signals from said two electrodes according to a standard limb lead method.

2. A method according to claim 1, wherein said electrodes are spaced from each other within a range of 1 to 7.5 cm.

3. A method according to claim 1, wherein said electrodes are spaced from each other in a range of 2 to 7.5 cm.

4. A method of detecting a ECG wave of a subject, comprising:
    (a) positioning two electrodes within 2.5 cm of an area defined by a first or second intercostal space sternal border parallel to a clavicle through a midclavicular on the subject's left chest; and (b) detecting a ECG wave from signals from said two electrodes according to a standard limb lead method.

5. A method according to claim 4, wherein said electrodes are spaced from each other within a range of 1 to 7.5 cm.

6. A method according to claim 4, wherein said electrodes are spaced from each other in a range of 2 to 7.5 cm.

7. A method of detecting a ECG wave of a subject, using a ECG signal transmission apparatus which comprises: two electrodes for detecting a ECG signal; a support for supporting said electrodes, said support operative to be placed on a living body; a transmitter having an electric circuit for processing the ECG signal detected on said electrodes; said method comprising:

(a) positioning said two electrodes within a first or second intercostal space sternal border parallel to a clavicle;

(b) detecting a ECG wave from signals from said two electrodes according to a standard limb lead method.

8. A method of detecting a ECG wave of a subject, using a ECG signal transmission apparatus which comprises: two electrodes for detecting a ECG signal; a support for supporting said electrodes, said support operative to be placed on a living body; a transmitter having an electric circuit for processing the ECG signal detected on said electrodes; said method comprising:

(a) positioning said two electrodes within a first or second intercostal space sternal border parallel to a clavicle through a midclavicular on the subject's left chest;

(b) detecting a ECG wave from signals from said two electrodes according to a standard limb lead method.

9. A method according to claim 8, wherein said electrodes are spaced from each other within a range of 1 to 7.5 cm.

10. A method according to claim 8, wherein said electrodes are spaced from each other in a range of 2 to 7.5 cm.

* * * * *